(12) United States Patent
Cohen et al.

(10) Patent No.: US 8,748,459 B2
(45) Date of Patent: *Jun. 10, 2014

(54) PYRIDINOYLPIPERIDINES AS 5-HT$_{1F}$ AGONISTS

(75) Inventors: Michael Philip Cohen, Indianapolis, IN (US); Daniel Timothy Kohlman, Camby, IN (US); Sidney Xi Liang, Bethany, CT (US); Frantz Victor, Indianapolis, IN (US); Yao-Chang Xu, Fishers, IN (US); Bai-Ping Ying, Sunnyvale, CA (US); DeAnna Piatt Zacherl, Noblesville, IN (US); Deyi Zhang, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/363,895

(22) Filed: Feb. 1, 2012

(65) Prior Publication Data
US 2012/0329820 A1 Dec. 27, 2012

Related U.S. Application Data

(63) Continuation of application No. 12/221,919, filed on Aug. 7, 2008, now abandoned, which is a continuation of application No. 10/509,770, filed as application No. PCT/US03/08455 on Mar. 27, 2003, now Pat. No. 7,423,050.

(60) Provisional application No. 60/369,088, filed on Mar. 29, 2002.

(51) Int. Cl.
*A61K 31/445* (2006.01)
*C07D 401/06* (2006.01)

(52) U.S. Cl.
USPC .......................... 514/318; 546/193

(58) Field of Classification Search
USPC .......................... 514/318; 546/193
See application file for complete search history.

(56) References Cited

U.S. PATENT DOCUMENTS

| | | | |
|---|---|---|---|
| 5,011,472 A | 4/1991 | Aebischer et al. | |
| 5,023,252 A | 6/1991 | Hseih | |
| 5,385,912 A | 1/1995 | Neuenschwander et al. | |
| 5,521,196 A | 5/1996 | Audia et al. | |
| 5,521,197 A | 5/1996 | Audia | |
| 5,698,571 A | 12/1997 | Audia et al. | |
| 5,708,008 A | 1/1998 | Audia et al. | |
| 5,708,187 A | 1/1998 | Flaugh et al. | |
| 5,721,252 A | 2/1998 | Audia et al. | |
| 5,814,653 A | 9/1998 | Flaugh et al. | |
| 5,817,671 A | 10/1998 | Filla et al. | |
| 6,528,529 B1 | 3/2003 | Brann et al. | |
| 6,650,463 B2 | 11/2003 | Obikawa et al. | |
| 6,777,428 B1 | 8/2004 | Krushinski, Jr. et al. | |
| 7,291,632 B2 | 11/2007 | Blanco-Pillado et al. | |
| 7,423,050 B2* | 9/2008 | Cohen et al. ............ | 514/318 |
| 7,608,629 B2 | 10/2009 | Blanco-Pillado et al. | |

(Continued)

FOREIGN PATENT DOCUMENTS

| | | |
|---|---|---|
| JP | 03255426 A | 11/1991 |
| KR | 2006-0067738 A | 6/2006 |

(Continued)

OTHER PUBLICATIONS

Streitwieser et al. "Metallation." *Introduction to Organic Chemistry*. eds. Upper Saddie River, NJ: Prentice Hall. (1992):1011-1012.

(Continued)

*Primary Examiner* — Celia Chang
(74) *Attorney, Agent, or Firm* — Mintz Levin Cohn Ferris Glovsky and Popeo, P.C.

(57) ABSTRACT

The present invention relates to compounds of formula I:

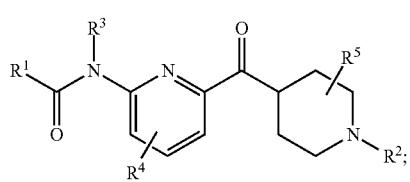

I or pharmaceutically acceptable acid addition salts thereof, where;

$R^1$ is $C_1$-$C_6$ alkyl, substituted $C_1$-$C_6$ alkyl, $C_3$-$C_7$ cycloalkyl, substituted $C_3$-$C_7$ cycloalkyl, $C_3$-$C_7$ cycloalkyl-$C_1$-$C_3$ alkyl, substituted $C_3$-$C_7$ cycloalkyl-$C_1$-$C_3$ alkyl, phenyl, substituted phenyl, heterocycle, or substituted heterocycle;

$R^2$ is hydrogen, $C_1$-$C_3$ alkyl, $C_3$-$C_6$ cycloalkyl-$C_1$-$C_3$ alkyl, or a group of formula II

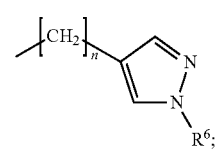

II $R^3$ is hydrogen or $C_1$-$C_3$ alkyl;
$R^4$ is hydrogen, halo, or $C_1$-$C_3$ alkyl;
$R^5$ is hydrogen or $C_1$-$C_3$ alkyl;
$R^6$ is hydrogen or $C_1$-$C_6$ alkyl; and
n is an integer from 1 to 6 inclusively.

The compounds of the present invention are useful for activating 5-HT$_{1F}$ receptors, inhibiting neuronal protein extravasation, and for the treatment or prevention of migraine in a mammal. The present invention also relates to a process for the synthesis of intermediates in the synthesis of compounds of Formula I.

3 Claims, No Drawings

(56) References Cited

U.S. PATENT DOCUMENTS

| | | | |
|---|---|---|---|
| 2002/0175891 | A1 | 11/2002 | Obikawa et al. |
| 2003/0144285 | A1 | 7/2003 | Brann et al. |
| 2003/0175445 | A1 | 9/2003 | Kirsch et al. |
| 2005/0009871 | A1 | 1/2005 | Ramesh et al. |
| 2005/0080112 | A1 | 4/2005 | Madsen et al. |
| 2006/0211734 | A1 | 9/2006 | Blanco-Pillado et al. |
| 2007/0129354 | A1 | 6/2007 | Aston et al. |
| 2007/0219187 | A1 | 9/2007 | Bessis et al. |
| 2007/0299110 | A1 | 12/2007 | Gagliardi et al. |
| 2008/0300407 | A1 | 12/2008 | Cohen et al. |
| 2010/0256187 | A1 | 10/2010 | Pilgrim et al. |

FOREIGN PATENT DOCUMENTS

| | | | |
|---|---|---|---|
| WO | WO-9314201 | A1 | 7/1993 |
| WO | WO-9629075 | A1 | 9/1996 |
| WO | WO-9713512 | A1 | 4/1997 |
| WO | WO-9808502 | A1 | 3/1998 |
| WO | WO-9815545 | A1 | 4/1998 |
| WO | WO-9820875 | A1 | 5/1998 |
| WO | WO-9846570 | A1 | 10/1998 |
| WO | WO-9855115 | A1 | 12/1998 |
| WO | WO-9925348 | A1 | 5/1999 |
| WO | WO-0000487 | A1 | 1/2000 |
| WO | WO-0000490 | A2 | 1/2000 |
| WO | WO-0034266 | A1 | 6/2000 |
| WO | WO-0047559 | A2 | 8/2000 |
| WO | WO-0050426 | A2 | 8/2000 |
| WO | WO-0105763 | A2 | 1/2001 |
| WO | WO-0206196 | A1 | 1/2002 |
| WO | WO-03/000245 | A1 | 1/2003 |
| WO | WO-03084949 | A1 | 10/2003 |
| WO | WO-2004047739 | A2 | 6/2004 |
| WO | WO-2004089874 | A1 | 10/2004 |
| WO | WO-2004099127 | A1 | 11/2004 |
| WO | WO-2005007621 | A2 | 1/2005 |
| WO | WO-2005/044797 | A1 | 5/2005 |
| WO | WO-2006048771 | A1 | 5/2006 |
| WO | WO-2006058905 | A1 | 6/2006 |
| WO | WO-2006081127 | A2 | 8/2006 |
| WO | WO-2006108487 | A1 | 10/2006 |
| WO | WO-2008114971 | A1 | 9/2008 |
| WO | WO-2011123654 | A1 | 10/2011 |

OTHER PUBLICATIONS

Pringsheim et al. "Prophylaxis of Migraine Headache". *CMAJ*. 182.7(2010):E269-276.

"A Placebo-Controlled Adaptive Treatment Assignment Study of Intravenous COL-144 in the Acute Treatment of Migraine." Study 2 of 2 for search of: CoLucid, *Clinical Trials*, Oct. 4, 2006.

King, F. D. "Bioisosteres, Conformational Restriction, and Prodrugs—Case History: An Example of a Conformational Restriction Approach." *Medicinal Chemistry: Principles and Practice*, Royal Society of Chemistry, Cambridge, England, Ch. 14 (1994) : 206-209.

Adham et al. "Cloning of another human serotonin receptor (5-HT$_{1F}$): A fifth 5-HT$_1$ receptor subtype coupled to the inhibition of adenylate cyclase." *Proc. Natl. Acad. Sci. USA* 90 (1993) : 408-412.

Phebus et al. "Characterization of LY344864 as a Pharmacological Tool to Study 5-HT1F Receptors: Binding Affinities, Brain Penetration and Activity in the Neurogenic Dural Inflammational Model of Migraine." CA 128:18603, *Life Sciences* 61.21 (1997) : 2117-2126.

Radl et al. "Synthesis and Antinociceptive Activity of Some 3-Chlorophenyl- and 6-Chloro-2-Pyridinyl Derivatives." CA 130:352171, *Collection of Czechoslovak Chemical Communications* 64.2 (1999) : 377-388.

"Dose-ranging Study of Oral COL-144 in Acute Migraine Treatmen—Study 1 of 2 for search of: Colucid", Clinical Trials, Apr. 16, 2009 (5 pages).

Berge et al. "Pharmaceutical Salts." *J. Pharm. Sci.* 66.1(1977):1-19.

Diener et al. "The Importance of Placebo in Headache Research." *Cephalalgia*. 28.10(2008):1003-1011.

Ferrari et al. "Oral Triptans (Serotonin 5-HT1B/1D Agonists) in Acute Migraine Treatment: A Meta-Analysis of 53 Trials." *Lancet*. 358(2001):1668-1675.

Goadsby et al. "Migraine—Current Understanding and Treatment." *N. Engl. J. Med*. 346.4(2002):257-270.

Goldstein et al. "Selective Seratonin 1F (5-HT1F) Receptor Agonist LY334370 for Acute Migraine: A Randomised Controlled Trial." *Lancet*. 358.9289(2001):1230-1234.

Graham et al. "Mechanism of Migraine Headache and Action of Ergotamine Tartrate." *Arch. Neurol. Psychaitry*. 39.4(1938):737-763.

Gros et al. "Aggregative Activation in Heterocyclic Chemistry. Part 5. Lithiation of Pyridine and Quinoline with the Complex Base BuLi-Me2N(CH2)2OLi (BuLi-LiDMAE)." *J. Chem. Soc., Perkin Trans*. 1. 24(1997):3597-3600.

Hall et al. "A Group Sequential Adaptive Treatment Assignment Design for Proof of Concept and Dose Selection in Headache Trials." *Contemp. Clin. Trials*. 26.3(2005):349-364.

Headache Classification Subcommittee of the International Headache Society. "The International Classification of Headache Disorders: Second Edition." *Cephalalgia*. 24.S11(2004):1-160.

Herrick-Davis et al. "Detection and Characterization of the Serotonin 5-HT 1D Receptor in Rat and Human Brain." *J. Neurochem*. 50.5(1988):1624-1631.

Ho et al. "Efficacy and Tolerability of MK-0974 (telcagepant), a New Oral Antagonist of Calcitonin Gene-Related Peptide Receptor, Compared with Zolmitriptan for Acute Migraine: A Randomised, Placebo-Controlled, Parallel-Treatment Trial." *Lancet*. 372.9656(2008):2115-2123.

Humphrey et al. "Serotonin and Migraine." *Ann. N.Y. Acad. Sci.* 600(1990):587-598.

International Headache Society Clinical Trials Subcommittee. "Guidelines for Controlled Trials of Drugs in Migraine: Second Edition." *Cephalalgia*. 20.9(2000):765-786.

MaassenVanDenBrink et al. "Coronary Side-Effect Potential of Current and Prospective Antimigraine Drugs." *Circulation*. 98.1(1998):25-30.

Moskowitz. "Interpreting Vessel Diameter Changes in Vascular Headaches." *Cephalalgia*. 12.1(1992):5-7.

Moskowitz. "Neurogenic Inflammation in the Pathophysiology and Treatment of Migraine." *Neurol*. 43.S3(1993):S16-S20.

Nelson et al. COL-144: Preclinical Profile of a Selective 5-HT1F Receptor Agonist for Migraine. *Cephalalgia*. 29(2009):122-123. (Abstract # PC.12).

Olesen et al. "Calcitonin Gene-Related Peptide Receptor Antagonist BIBN 4096 BS for the Acute Treatment of Migraine." *N. Engl. J. Med*. 350.11(2004):1104-1110.

Schoonman et al. "Migraine Headache is not Associated with Cerebral of Meningeal Vasodilation—a 3 T Magnetic Resonance Angiography Study." *Brain*. 131.Pt8(2008):2192-2200.

Stovner et al. "The Global Burden of Headache: A Documentation of Headache Prevalence and Disablity Worldwide." *Cephalalgia*. 27.3(2007):193-210.

Visser et al. "Chest Symptoms After Sumatriptan: A Two-Year Clinical Practice Review in 735 Consecutive Migraine Patients." *Cephalalgia*. 16.8(1996):554-559.

Weinshank et al. "Human Serotonin 1D Receptor is Encoded by a Subfamily of Two Distinct Genes: 5-HT1Dα and 5-HT1Dβ." *PNAS*. 89.8(1992):3630-3634.

Welch et al. "Tolerability of Sumatriptan: Clinical Trials and Post-Marketing Experience." *Cephalalgia*. 20.8(2000):687-695.

\* cited by examiner

PYRIDINOYLPIPERIDINES AS 5-HT$_{1F}$ AGONISTS

RELATED APPLICATIONS

This application is a continuation and claims the benefit of priority under 35 U.S.C. 120 to U.S. non-provisional application Ser. No. 12/221,919, filed Aug. 7, 2008, which is a continuation of U.S. non-provisional application Ser. No. 10/509,770, filed Sep. 28, 2004, now U.S. Pat. No. 7,423,050, which is a U.S. national stage application, filed under 35 U.S.C. 371, of International Application PCT/US03/08455, filed Mar. 27, 2003, which claims priority to U.S. provisional Application No. 60/369,088, filed Mar. 29, 2002, the disclosures of each of which are incorporated by reference herein in their entireties.

BACKGROUND OF THE INVENTION

Until recently, theories regarding the pathophysiology of migraine have been dominated since 1938 by the work of Graham and Wolff. *Arch. Neurol. Psychiatry*, 39:737-63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, induce contraction of cephalic vascular smooth muscle and are effective in the treatment of migraine. Humphrey, et al., *Ann. NY Acad. Sci.*, 600:587-600, 1990. Recent work by Moskowitz has shown, however, that the occurrence of migraine headaches is independent of changes in vessel diameter. *Cephalalgia*, 12:5-7, 1992.

Moskowitz has proposed that currently unknown triggers for pain stimulate trigeminal ganglia that innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16-S20 1993. Sumatriptan, in fact, has high affinity for the 5-HT$_{1B}$ and 5-HT$_{1D}$ receptors, Ki=10.3 nM and 5.1 nM, respectively, which activity may be indicative of vasoconstrictive activity. Sumatriptan and similar compounds previously advanced for the treatment of migraine had tended to be selected on the basis of this vasoconstrictive activity under the premises of the prior art models for migraine.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408-412, 1993. This 5-HT$_{1F}$ receptor exhibits a pharmacological profile distinct from any serotonergic receptor yet described. It was found that sumatriptan, in addition to the above mentioned strong affinities for the 5-HT$_{1B}$ and 5-HT$_{1D}$ receptors, also has affinity for this receptor subtype, with a K$_i$ of about 23 nM. This suggests a possible role of the 5-HT$_{1F}$ receptor in migraine.

Various 5-HT$_{1F}$ receptor agonists have subsequently been developed which have shown relative selectivity for the 5-HT$_{1F}$ receptor subclass and it has been shown that such selectivity generally reduces the vasoconstrictive activity characteristic of other compounds advanced as potential agents for the treatment of migraine and associated disorders.

Included among these 5-HT$_{1F}$ receptor agonists are compounds disclosed in the following:

- U.S. Pat. Nos. 5,708,187 and 5,814,653, describing a family of 6-substituted-3-amino(alkyl)-tetrahydrocarbazoles and 7-substituted-4-amino(alkyl)cyclohepta[7,6b]indoles;
- U.S. Pat. Nos. 5,521,196, 5,721,252, 5,521,197, and WO 96/29075, describing various families of 5-substituted piperidin-3-yl-indoles and 5-substituted 1,2,3,6 tetrahydropyridin-3-yl-indoles;
- WO 97/13512 describing a family of 5-substituted 3-aminoethylindoles;
- WO 98/46570 describing a family of 5-substituted indoles, pyrrolo[3,2-b]pyridines, benzofurans, and benzothiophenes, having the 3-position substituted with octahydroindolizinyl, octahydro-2H-quinolizinyl, decahydropyrido[1,2-a]azepinyl, 1,2,3,5,8,8a-hexahydroindolizinyl, 1,3,4,6,9,9a-hexahydro-2H-quinolizinyl, or 1,4,6,7,8,9,10,10a-octahydropyrido[1,2-a]azepinyl;
- WO 98/20875 and WO 99/25348 describing two families of 5-substituted piperidin-3-yl-azaindoles and 5-substituted 1,2,3,6-tetrahydropyridin-3-yl-azaindoles;
- WO 00/00487 describing a family of 5-substituted (piperidin-3-yl or 1,2,3,6-tetrahydropyridin-3-yl)indoles, azaindoles, benzofurans, and benzothiophenes;
- WO 98/08502 describing a family of 8-substituted-1,2,3,4-tetrahydro-2-dibenzofuranamines and 9-substituted-2-aminocyclohepta[b]benzofurans;
- WO 98/55115 describing a family of 3-amino-1,2,3,4-tetrahydro-9H-carbazole-6-carboxamides and 4-amino-10H-cyclohepta[7,6-b]indole-7-carboxamides;
- WO 98/15545 describing a select family of 3,5-disubstituted indoles and benzofurans;
- WO 00/00490 describing a family of 5-allyl-substituted (piperidin-3-yl or 1,2,3,6-tetrahydropyridin-3-yl)indoles, azaindoles, benzofurans, and benzothiophenes;
- WO 00/47559 describing a family of 4-(3-substituted-benzoyl)piperidines;
- WO 00/50426 describing a family of 3,5-disubstituted azabenzofurans; and
- WO 00/34266 describing a family of 3-heteroaryl-5-[2-(aryl or heteroaryl)-2-oxoethyl]indoles.

Continued research has now surprisingly yielded a new and unexpected class of novel selective 5-HT$_{1F}$ agonists having distinct chemical and receptor binding properties, which inhibit peptide extravasation, while avoiding significant vasoconstrictive activity, and are therefore useful for the treatment of migraine and other 5-HT$_{1F}$ receptor associated disorders. Furthermore, the compounds of the present invention may provide improved solubility, which facilitates suitability in preferred formulations, such as sublingual, buccal, and/or nasal formulations.

SUMMARY OF THE INVENTION

The present invention relates to pyridinoylpiperidine compounds of the general formula I:

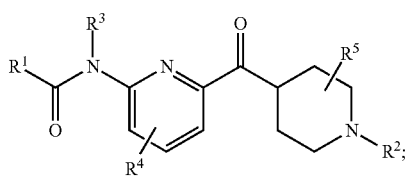

and pharmaceutically acceptable acid addition salts thereof, where;

$R^1$ is $C_1$-$C_6$ alkyl, substituted $C_1$-$C_6$ alkyl, $C_3$-$C_7$ cycloalkyl, substituted $C_3$-$C_7$ cycloalkyl, $C_3$-$C_7$ cycloalkyl-$C_1$-$C_3$ alkyl, substituted $C_3$-$C_7$ cycloalkyl-$C_1$-$C_3$ alkyl, phenyl, substituted phenyl, heterocycle, or substituted heterocycle;

$R^2$ is hydrogen, $C_1$-$C_3$ alkyl, $C_3$-$C_6$ cycloalkyl-$C_1$-$C_3$ alkyl, or a group of formula II

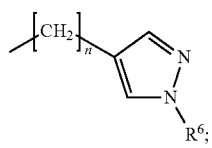

$R^3$ is hydrogen or $C_1$-$C_3$ alkyl;
$R^4$ is hydrogen, halo, or $C_1$-$C_3$ alkyl;
$R^5$ is hydrogen or $C_1$-$C_3$ alkyl;
$R^6$ is hydrogen or $C_1$-$C_6$ alkyl; and
n is an integer from 1 to 6 inclusively.

In one preferred embodiment, the present invention relates to pyridinoylpiperidine compounds of the general formula I:

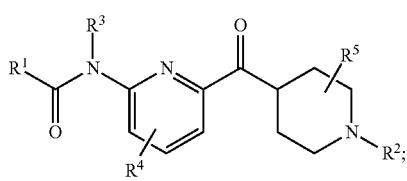

and pharmaceutically acceptable acid addition salts thereof, wherein;

$R^1$ is phenyl, substituted phenyl, heterocycle or substituted heterocycle;
$R^2$ is hydrogen or $C_1$-$C_2$ alkyl;
$R^3$ is hydrogen or methyl; and
$R^4$ and $R^5$ are both hydrogen.

Other preferred compounds are those of formula I wherein $R^3$ is hydrogen.

This invention also relates to pharmaceutical formulations comprising a compound of formula I, or a pharmaceutically acceptable acid addition salt thereof, and a pharmaceutical carrier, diluent, or excipient. In preferred embodiments of this aspect of the present invention, there are provided pharmaceutical formulations containing a compound of formula I, or a pharmaceutically acceptable salt thereof, adapted for the activation of 5-$HT_{1F}$ receptors, for the inhibition of neuronal protein extravasation, for the treatment or prevention of migraine, and/or the treatment or prevention of anxiety in mammals, particularly humans.

In addition, the present invention relates to a method for activating 5-$HT_{1F}$ receptors in mammals, particularly humans, comprising administering to a mammal in need of such activation an effective amount of a compound of formula I, or a pharmaceutically acceptable acid addition salt thereof.

Moreover, the current invention relates to a method for inhibiting neuronal protein extravasation in mammals, particularly humans, comprising administering to a mammal in need of such inhibition an effective amount of a compound of formula I, or a pharmaceutically acceptable acid addition salt thereof.

Additionally, the present invention relates to a method for treating or preventing migraine in mammals, particularly humans, comprising administering to a mammal in need of such treatment or prevention, an effective amount of a compound of formula I, or a pharmaceutically acceptable acid addition salt thereof.

Additionally, the present invention relates to a method for treating anxiety in mammals, particularly humans, comprising administering to a mammal in need of such treatment or prevention, an effective amount of a compound of formula I, or a pharmaceutically acceptable acid addition salt thereof.

In another aspect, the present invention relates to a compound of formula I, or a pharmaceutically acceptable acid addition salt thereof, for use in the activation of 5-$HT_{1F}$ receptors, in the inhibition of neuronal protein extravasation, in the treatment or prevention of migraine, and/or in the treatment of anxiety in mammals, particularly humans. That is to say, the present invention relates to the use of a compound of formula I as a medicament for the activation of 5-$HT_{1F}$ receptors, for the inhibition of neuronal protein extravasation, for the treatment or prevention of migraine, and/or for the treatment of anxiety in mammals, particularly humans.

Additionally, the present invention relates to the use of one or more compounds of formula I in the manufacture of a medicament for the activation of 5-$HT_{1F}$ receptors, for the inhibition of neuronal protein extravasation, for the treatment or prevention of migraine, and/or for the treatment of anxiety in mammals, particularly humans.

Furthermore, the present invention provides for methods for the treatment of 5-$HT_{1F}$ mediated disorders comprising administering to a mammal in need of such treatment, particularly a human, an effective amount of a compound of formula I, or a pharmaceutically acceptable acid addition salt thereof.

In another aspect of the present invention, there is provided a process for the synthesis of compounds of formula I and of novel intermediates in the synthesis. In one embodiment, the present invention provides a process for preparing a 2-halo-6-(piperidin-4-carbonyl)pyridine compound of formula III

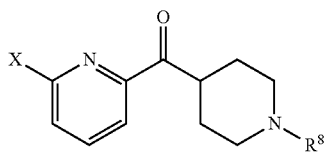

III where X is bromo or chloro;
R$^8$ is an amino protecting group, C$_1$-C$_3$ alkyl, C$_3$-C$_6$ cycloalkyl-C$_1$-C$_3$ alkyl, or a group of formula II

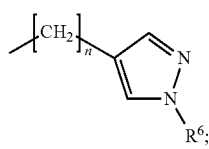

II

R$^6$ is hydrogen or C$_1$-C$_6$ alkyl; and
n is an integer from 1 to 6 inclusively;
comprising
1) reacting a 2,6-dihalopyridine selected from the group consisting of 2,6-dibromopyridine and 2,6-dichloropyridine, with n-butyl lithium to form 2-halo-6-lithium-pyridine; and then
2) reacting the 2-halo-6-lithium-pyridine with a substituted aminocarbonylpiperidine compound of formula IV

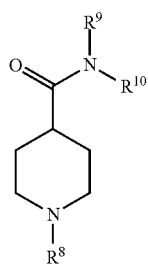

IV wherein R$^9$ and R$^{10}$ are each methyl, or R$^9$ and R$^{10}$, together with the nitrogen to which they are attached, combine to form azetidinyl, pyrrolidinyl, or piperidinyl.

In a particular embodiment of this aspect of the present invention, there is provided a process for preparing a 2-bromo-6-(piperidin-4-carbonyl)pyridine compound of formula III

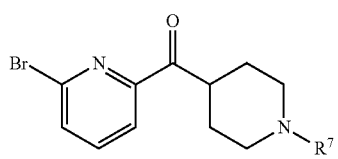

III wherein R$^7$ is C$_1$-C$_3$ n-alkyl, or an amino protecting group; comprising reacting 2,6-dibromopyridine with n-butyl lithium to form 2-bromo-6-lithium pyridine, and then reacting the 2-bromo-6-lithium pyridine with a 4-(N,N'-dimethylamino)carbonyl piperidine compound of formula IV

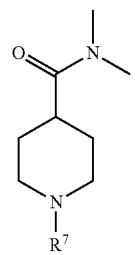

IV in a methyl tert-butyl ether solvent.

DETAILED DESCRIPTION OF THE INVENTION

One embodiment of the present invention is a method for increasing activation of 5-HT$_{1F}$ receptors, while avoiding vasoconstrictive activity, for treating a variety of disorders that have been linked to decreased neurotransmission of serotonin in mammals. Included among these disorders are migraine, general pain, trigeminal neuralgia, dental pain or temperomandibular joint dysfunction pain, anxiety, general anxiety disorder, panic disorder, depression, disorders of sleep, chronic fatigue syndrome, premenstrual syndrome or late luteal phase syndrome, post-traumatic syndrome, memory loss, dementia including dementia of aging, social phobia, autism, attention deficit hyperactivity disorder, disruptive behavior disorders, impulse control disorders, borderline personality disorder, obsessive compulsive disorder, premature ejaculation, erectile dysfunction, bulimia, anorexia nervosa, alcoholism, tobacco abuse, mutism, and trichotillomania. The compounds of this invention are also useful as a prophylactic treatment for migraine. Any of these methods employ a compound of formula I.

In those instances where the disorders which can be treated by serotonin agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The use of a compound of formula I for the activation of the 5-HT$_{1F}$ receptor, for the inhibition of neuronal peptide extravasation, in general or due to stimulation of the trigeminal ganglia specifically, and/or for the treatment of any of the disorders described above, are all embodiments of the present invention.

Likewise, the use of a compound of formula I, or a combination of more than one compound of formula I, in the manufacture of a medicament for the activation of the 5-HT$_{1F}$ receptor, for the inhibition of neuronal peptide extravasation, in general or due to stimulation of the trigeminal ganglia specifically, and/or for the treatment of any of the disorders described above, are also all embodiments of the present invention. The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_4$ alkyl" refers to a straight chain or branched hydrocarbon moiety having from 1 to 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties having from 1 to 4 carbon atoms including methyl, ethyl, n-propyl, and n-butyl. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted as specified herein.

The terms "alkoxy", "phenyloxy", "benzoxy" and "pyrimidinyloxy" refer to an alkyl group, phenyl group, benzyl group, or pyrimidinyl group, respectively, each optionally substituted, that is bonded through an oxygen atom.

The terms "alkylthio", "phenylthio", and "benzylthio" refer to an alkyl group, phenyl group, or benzyl group, respectively, each optionally substituted, that is bonded through a sulfur atom.

The term "$C_1$-$C_4$ acyl" refers to a formyl group or a $C_1$-$C_3$ alkyl group bonded through a carbonyl moiety. The term "$C_1$-$C_4$ alkoxycarbonyl" refers to a $C_1$-$C_4$ alkoxy group bonded through a carbonyl moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 5- or 6-membered ring containing from 1 to 3 heteroatoms selected from nitrogen, oxygen and sulfur, said ring optionally being benzofused. Exemplary heterocycles, for the purposes of the present invention, include furanyl, thiophenyl (thienyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

Preferred heterocycles include pyridinyl, indolyl, furanyl, benzofuranyl, thiophenyl, benzodioxolyl, and thiazolidinyl, all of which may be optionally substituted.

Substituted alkyl, cycloalkyl, cycloalkylalkyl, alkoxy, or alkylthio, means an alkyl, cycloalkyl, cycloalkylalkyl, alkoxy, or alkylthio group, respectively, substituted one or more times independently with a substituent selected from the group consisting of halo, hydroxy, and $C_1$-$C_3$ alkoxy. By way of illustration, but without limitation, examples include trifluoromethyl, pentafluoroethyl, 5-fluoro-2-bromopentyl, 3-hydroxypropyloxy, 4-hydroxycyclohexyloxy, 2-bromoethylthio, 3-ethoxypropyloxy, 3-ethoxy-4-chlorocyclohexyl, and the like. Preferred substitutions include substitution 1-5 times with halo, each independently selected, or substituted 1-3 times with halo and 1-2 times independently with a group selected from hydroxy and $C_1$-$C_3$ alkoxy, or substituted 1-3 times independently with a group selected from hydroxy and $C_1$-$C_3$ alkoxy, provided that no more than one hydroxy and/or alkoxy substituent may be attached through the same carbon.

The terms "substituted phenyl" and "substituted heterocycle" are taken to mean that the cyclic moiety in either case is substituted with one or more halo substituents, preferably one to five, each independently selected; or substituted with one or more substituents, preferably one to two substituents, independently selected from the group consisting of halo, $C_1$-$C_4$ alkyl, $C_1$-$C_4$ alkoxy, and $C_1$-$C_4$ alkylthio, wherein each alkyl, alkoxy and alkylthio substituent can be further substituted independently with $C_1$-$C_2$ alkoxy or with one to five halo groups selected from fluoro and chloro; or substituted with one substituent selected from the group consisting of phenyloxy, benzyloxy, phenylthio, benzylthio, and pyrimidinyloxy, wherein the phenyloxy, benzyloxy, phenylthio, benzylthio, and pyrimidinyloxy moiety can be further substituted with one to two substituents selected from the group consisting of halo, $C_1$-$C_2$ alkyl, and $C_1$-$C_2$ alkoxy; or substituted with one substituent selected from the group consisting of $C_1$-$C_4$ acyl and $C_1$-$C_4$ alkoxycarbonyl, and further substituted with zero to one substituent selected from the group consisting of halo, $C_1$-$C_4$ alkyl, $C_1$-$C_4$ alkoxy, and $C_1$-$C_4$ alkylthio. When a substituent is halo, preferred halo groups are fluoro, chloro, and bromo.

$Pd_2(dba)_3$ means tris(dibenzylidineacetone)-dipalladium (0).

BINAP means 2,2'-bis(diphenylphosphino)-1,1'binaphthyl.

DMF means N,N-dimethylformamide.

HATU means O-(7-Azabenzotriazol-1-yl)-N,N,N',N'-tetramethyluronium hexafluorophosphate.

Collidine means trimethylpyridine.

HRMS means High Resolution Mass Spectrum.

CIMS means Chemical Ionization Mass Spectrum.

APCI MS means Atmospheric Pressure Chemical Ionization Mass Spectrum.

The term "amino protecting group" as used in this specification refers to a substituents commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivatized amino group is stable to the conditions of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as "Greene".

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipients and salt must be compatible with the active ingredient of the formulation (e.g. a compound of formula I). It is understood by those of ordinary skill in this art that the terms "pharmaceutical formulation" and "pharmaceutical composition" are generally interchangeable, and they are so used for the purposes of this application.

The term "acid addition salt" refers to a salt of a compound of formula I prepared by reaction of a compound of formula I with a mineral or organic acid. For exemplification of pharmaceutically acceptable acid addition salts see, e.g., Berge, S. M, Bighley, L. D., and Monkhouse, D.C., *J. Pharm. Sci.*, 66:1, 1977. Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature.

The pharmaceutically acceptable acid addition salts of the invention are typically formed by reacting a compound of formula I with an equimolar or excess amount of acid. Alternatively, hemi-salts can be formed by reacting a compound of formula I with the desired acid in a 2:1 ratio, compound to acid. The reactants are generally combined in a mutual solvent such as diethylether, tetrahydrofuran, methanol, ethanol, isopropanol, benzene, or the like. The salts normally precipitate out of solution within about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid and succinic acid.

The term "effective amount" means an amount of a compound of formula I which is capable of activating 5-HT$_{1F}$ receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

All enantiomers, diastereomers, and mixtures thereof, are included within the scope of the present invention. For example, the compounds of formula I wherein $R^5$ is other than hydrogen contain two chiral centers, one at the 4-position of the piperidine ring, and one where $R^5$ attaches to the piperidine ring. By way of illustration, but without limitation, the four stereoisomers of N-[6-(1,2-dimethylpiperidine-4-carbonyl)-pyridin-2-yl]-isonicotinamide are as follows, wherein the chiral centers are indicated with asterisks, "*", and the R and S designations are as indicated.

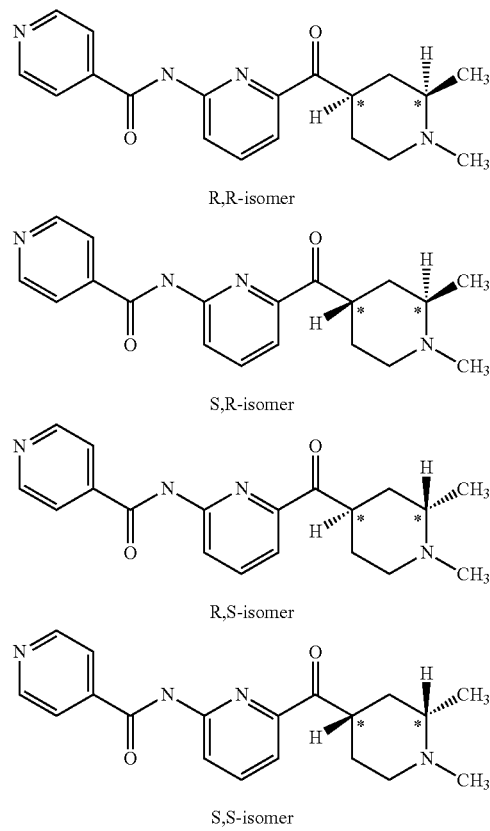

While all enantiomers, diastereomers, and mixtures thereof, are useful as 5-HT$_{1F}$ agonists, single enantiomers and single diastereomers are preferred. Furthermore, while all of the compounds of this invention are useful as 5-HT$_{1F}$ agonists, certain classes are preferred. The following paragraphs describe such preferred classes.

1) $R^1$ is phenyl, substituted phenyl, heterocycle, or substituted heterocycle;
2) $R^1$ is substituted phenyl;
3) $R^1$ is mono- or di-substituted phenyl wherein the substituents are independently selected from halo, $C_1$-$C_4$ alkyl, $C_1$-$C_4$ alkoxy, trifluoromethyl, trifluoromethoxy, trifluoroethoxy, phenyloxy, and benzyloxy;
4) $R^1$ is mono- or di-substituted phenyl wherein the substituents are independently selected from halo, $C_1$-$C_2$ alkoxy, trifluoromethyl, trifluoromethoxy, and trifluoroethoxy;
5) $R^1$ is di- or tri-halo substituted phenyl;
6) $R^1$ is heterocycle or substituted heterocycle;
7) $R^1$ is a substituted or unsubstituted heterocycle selected from the group consisting of furanyl, thiophenyl, pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, isoquinolinyl, benzoxazolyl, benzodioxolyl, benzothiazolyl, quinolinyl, benzofuranyl, benzothiophenyl, indolyl;
8) $R^1$ is a substituted or unsubstituted heterocycle selected from the group consisting of pyridinyl, indolyl, benzofuranyl, furanyl, thiophenyl, benzodioxolyl, and thiazolidinyl;
9) $R^1$ is a substituted or unsubstituted heterocycle selected from the group consisting of pyridinyl, furanyl, thiophenyl;

10) R$^1$ is mono-, di-, or tri-halo-substituted heterocycle, each halo group being independently selected;
11) R$^1$ is mono- or di-substituted heterocycle, wherein one of the substituents is selected from the group consisting of C$_1$-C$_2$ alkoxy, phenoxy, and phenylthio;
12) R$^2$ is hydrogen or C$_1$-C$_3$ alkyl;
13) R$^2$ is hydrogen or methyl;
14) R$^2$ is C$_3$-C$_6$ cycloalkyl-C$_1$-C$_3$ alkyl;
15) R$^2$ is pyrazolylalkyl or N-substituted pyrazolylalkyl;
16) R$^2$ is pyrazol-4-yl-ethyl;
17) R$^2$ is 1-(C$_1$-C$_3$ alkyl)pyrazol-4-yl-ethyl;
18) R$^3$ is hydrogen;
19) R$^3$ is methyl;
20) R$^3$ is ethyl;
21) R$^4$ is hydrogen;
22) R$^4$ is halo;
23) R$^4$ is fluoro or chloro;
24) R$^4$ is C$_1$-C$_3$ alkyl;
25) R$^4$ is methyl;
26) R$^5$ is hydrogen;
27) R$^5$ is C$_1$-C$_3$ alkyl;
28) R$^5$ is methyl;
29) R$^2$ is hydrogen or methyl, and R$^3$, R$^4$ and R$^5$ are all hydrogen;
30) R$^2$ is hydrogen or methyl, and R$^3$ is methyl, and R$^4$ and R$^5$ are both hydrogen;
31) R$^1$ is mono- or di-substituted phenyl wherein the substituents are independently selected from halo, C$_1$-C$_2$ alkoxy, trifluoromethyl, trifluoromethoxy, and trifluoroethoxy, R$^2$ is hydrogen or methyl, and R$^3$, R$^4$ and R$^5$ are hydrogen;
32) R$^1$ is a substituted or unsubstituted heterocycle selected from the group consisting of pyridinyl, indolyl, benzofuranyl, furanyl, thiophenyl, benzodioxolyl, and thiazolidinyl, R$^2$ is hydrogen or methyl, and R$^3$, R$^4$ and R$^5$ are hydrogen;
33) R$^1$ is substituted phenyl, R$^2$ is hydrogen or methyl, and R$^3$, R$^4$ and R$^5$ are all hydrogen;
34) R$^1$ is substituted phenyl, R$^2$ is hydrogen or methyl, and R$^3$ is methyl, and R$^4$ and R$^5$ are both hydrogen;
35) R$^1$ is mono- or di-substituted phenyl wherein the substituents are independently selected from halo, C$_1$-C$_2$ alkoxy, trifluoromethyl, trifluoromethoxy, and trifluoroethoxy, R$^2$ is hydrogen or methyl, R$^3$ is methyl and R$^4$ and R$^5$ are hydrogen;
36) R$^1$ is di- or tri-halo substituted phenyl, R$^2$ is hydrogen or methyl, and R$^3$, R$^4$ and R$^5$ are all hydrogen;
37) R$^1$ is di- or tri-halo substituted phenyl, R$^2$ is hydrogen or methyl, and R$^3$ is methyl, and R$^4$ and R$^5$ are both hydrogen;
38) R$^1$ is a substituted or unsubstituted heterocycle selected from the group consisting of pyridinyl, indolyl, benzofuranyl, furanyl, thiophenyl, benzodioxolyl, and thiazolidinyl, R$^2$ is hydrogen or methyl, R$^3$ is methyl, and R$^4$ and R$^5$ are hydrogen;
39) any compound exemplified;
40) the compound is an acid addition salt;
41) the compound is a hydrochloride salt;
42) the compound is the dihydrochloride salt.
43) the compound is the hemisuccinate salt;
44) the compound is the succinate salt; and
45) the compound is the disuccinate salt.

It will be understood that the above classes may be combined to form additional preferred classes, as for example the combination of preferred selections for two or more substituents. Illustrative examples of combinations of preferred classes forming additional preferred classes are:

46) the combination of any one of preferred classes 1), 2), 8) or 9) with preferred classes 21), and 26);
47) the combination of any one of preferred classes 1), 2), 8) or 9) with preferred classes 21), and 27);
48) the combination of any one of preferred classes 1), 2), 8) or 9) with preferred classes 21), and 28);
49) the combination of any one of preferred classes 1), 2), 8) or 9) with preferred classes 23), and 26);
50) the combination of any one of preferred classes 1), 2), 8) or 9) with preferred classes 23), and 28);
51) the combination of any one of preferred classes 1), 2), 8) or 9) with preferred classes 25), and 26);
52) the combination of any one of preferred classes 1), 2), 8) or 9) with preferred classes 25), and 28);
53) the combination of any one of the preferred combinations 46)-52) with preferred classes 12) and 18);
54) the combination of any one of the preferred combinations 46)-52) with preferred classes 12) and 19);
55) the combination of any one of the preferred combinations 46)-52) with preferred classes 13) and 18);
56) the combination of any one of the preferred combinations 46)-52) with preferred classes 13) and 19);
57) the combination of any one of the preferred combinations 46)-52) with preferred classes 14) and 18);
58) the combination of any one of the preferred combinations 46)-52) with preferred classes 14) and 19);
59) the combination of any one of the preferred combinations 46)-52) with preferred classes 15) and 18); and
60) the combination of any one of the preferred combinations 46)-52) with preferred classes 15) and 19).

In addition to those compounds presented in the examples, the following compounds further illustrate the scope of the present invention:

1) 4-Fluoro-N-[6(1-methyl-piperidine-4-carbonyl)-pyridin-2-yl]-benzamide;
2) 2,4-Difluoro-N-[6(1-methyl-piperidine-4-carbonyl)-pyridin-2-yl]-benzamide
3) N-[6(1-Methyl-piperidine-4-carbonyl)-pyridin-2-yl]-benzamide
4) 2-Chloro-4-fluoro-N-[6(1-methyl-piperidine-4-carbonyl)-pyridin-2-yl]-benzamide
5) 2-Chloro-N-[6(1-methyl-piperidine-4-carbonyl)-pyridin-2-yl]-benzamide
6) 2,4,6-Trifluoro-N-[6-(piperidine-4-carbonyl)-pyridin-2-yl]-benzamide
7) 1H-5-Trifluoromethyl-indole-3-carboxylic acid [6-(1-methyl-piperidine-4-carbonyl)-pyridin-2-yl]-amide
8) N-[6-(1-Methyl-piperidine-4-carbonyl)-pyridin-2-yl]-2-trifluoromethoxy-benzamide
9) 3-Bromo-thiophene-2-carboxylic acid [6-(1-methyl-piperidine-4-carbonyl)-pyridin-2-yl]-amide
10) 4-Fluoro-N-[6-(1-methyl-piperidine-4-carbonyl)-pyridin-2-yl]-2-trifluoromethyl-benzamide
11) 2,4,6-Trifluoro-N-[6-(1-methyl-piperidine-4-carbonyl)-pyridin-2-yl]-benzamide
12) 2-Chloro-6-fluoro-N-[6-(1-methyl-piperidine-4-carbonyl)-pyridin-2-yl]-benzamide
13) 2,4,6-Trifluoro-N-methyl-N-[6-(1-methyl-piperidine-4-carbonyl)-pyridin-2-yl]-benzamide
14) 2,4,6-Trifluoro-N-methyl-N-[6-(piperidine-4-carbonyl)-pyridin-2-yl]-benzamide
15) 2,4,6-Trifluoro-N-methyl-N-[6-(1-methyl-piperidine-4-carbonyl)-pyridin-2-yl]-benzamide
16) 2,4,6-Trifluoro-N-ethyl-N-[6-(1-methyl-piperidine-4-carbonyl)-pyridin-2-yl]-benzamide
17) 2-Chloro-4-fluoro-N-[6-(piperidin-4-carbonyl)-pyridin-2-yl]-benzamide 18) 2-Chloro-4-fluoro-N-methyl-N-[6-(1-methyl-piperidin-4-carbonyl)-pyridin-2-yl]-benzamide
19) 1H-5-Fluoro-indole-3-carboxylic acid [6-(1-methyl-piperidine-4-carbonyl)-pyridin-2-yl]-amide
20) Cyclopropanecarboxylic acid [6-(1-methyl-piperidine-4-carbonyl)-pyridin-2-yl]-amide
21) 3-Methyl-N-[6-(1-methyl-piperidine-4-carbonyl)-pyridin-2-yl]-butanamide
22) Thiophene-2-carboxylic acid [6-(1-methyl-piperidine-4-carbonyl)-pyridin-2-yl]-amide
23) Furan-2-carboxylic acid [6-(1-methyl-piperidine-4-carbonyl)-pyridin-2-yl]-amide
24) 2-Chloro-N-[6-(1-methyl-piperidine-4-carbonyl)-pyridin-2-yl]-benzamide
25) Furan-3-carboxylic acid [6-(1-methyl-piperidine-4-carbonyl)-pyridin-2-yl]-amide
26) 3,4-Difluoro-N-[6-(1-methyl-piperidine-4-carbonyl)-pyridin-2-yl]-benzamide
27) N-[6-(1-Methyl-piperidine-4-carbonyl)-pyridin-2-yl]-isonicotinamide
28) 2-Methyl-N-[6-(1-methyl-piperidine-4-carbonyl)-pyridin-2-yl]-benzamide
29) 2-Bromo-N-[6-(1-methyl-piperidine-4-carbonyl)-pyridin-2-yl]-benzamide
30) Thiophene-3-carboxylic acid [6-(1-methyl-piperidine-4-carbonyl)-pyridin-2-yl]-amide
31) 2-Fluoro-N-[6-(1-methyl-piperidine-4-carbonyl)-pyridin-2-yl]-isonicotinamide
32) 4-Chloro-2-methoxy-N-[6-(1-methyl-piperidine-4-carbonyl)-pyridin-2-yl]-benzamide
33) 2-Ethoxy-N-[6-(1-methyl-piperidine-4-carbonyl)-pyridin-2-yl]-benzamide
34) N-[6-(1-Methyl-piperidine-4-carbonyl)-pyridin-2-yl]-2-phenoxy-benzamide
35) 5-Chloro-2-methoxy-N-[6-(1-methyl-piperidine-4-carbonyl)-pyridin-2-yl]-benzamide
36) 2-Methoxy-N-[6-(1-methyl-piperidine-4-carbonyl)-pyridin-2-yl]-4-methylsulfanyl-benzamide
37) 2,3-Dihydro-benzofuran-7-carboxylic acid [6-(1-methyl-piperidine-4-carbonyl)-pyridin-2-yl]-amide
38) 2-Benzyloxy-N-[6-(1-methyl-piperidine-4-carbonyl)-pyridin-2-yl]-benzamide
39) N-[6-(1-Methyl-piperidine-4-carbonyl)-pyridin-2-yl]-2-propoxy-benzamide
40) 2,2-Difluoro-benzo[1,3]dioxole-4-carboxylic acid [6-(1-methyl-piperidine-4-carbonyl)-pyridin-2-yl]-amide
41) 4-Methoxy-2-(2-methoxy-ethoxy)-N-[6-(1-methyl-piperidine-4-carbonyl)-pyridin-2-yl]-benzamide
42) 5-Bromo-2-methoxy-N-[6-(1-methyl-piperidine-4-carbonyl)-pyridin-2-yl]-benzamide
43) 2-(4,6-Dimethoxy-pyrimidin-2-yloxy)-N-[6-(1-methyl-piperidine-4-carbonyl)-pyridin-2-yl]-benzamide
44) N-[6-(1-Methyl-piperidine-4-carbonyl)-pyridin-2-yl]-butanamide
45) Cyclohexanecarboxylic acid [6-(1-methyl-piperidine-4-carbonyl)-pyridin-2-yl]-amide
46) N-[6-(1-Methyl-piperidine-4-carbonyl)-pyridin-2-yl]-3-phenyl-propionamide
47) 2,6-Difluoro-N-[6-(1-methyl-piperidine-4-carbonyl)-pyridin-2-yl]-benzamide
48) 2-Ethoxy-N-[6-(1-methyl-piperidine-4-carbonyl)-pyridin-2-yl]-nicotinamide
49) N-[6-(1-Methyl-piperidine-4-carbonyl)-pyridin-2-yl]-2-phenoxy-nicotinamide
50) 3-Acetyl-thiazolidine-4-carboxylic acid [6-(1-methyl-piperidine-4-carbonyl)-pyridin-2-yl]-amide
51) N-[6-(1-Methyl-piperidine-4-carbonyl)-pyridin-2-yl]-2-phenylsulfanyl-nicotinamide
52) 5-Methoxy-N-[6-(1-methyl-piperidine-4-carbonyl)-pyridin-2-yl]-2-(2,2,2-trifluoro-ethoxy)-benzamide
53) 2-Methoxy-6-methyl-N-[6-(1-methyl-piperidine-4-carbonyl)-pyridin-2-yl]-benzamide
54) N-[6-(1-Methyl-piperidine-4-carbonyl)-pyridin-2-yl]-terephthalamic acid methyl ester
55) Cyclobutanecarboxylic acid [6-(1-methyl-piperidine-4-carbonyl)-pyridin-2-yl]-amide
56) 2-(2-Chloro-1,1,2-trifluoro-ethoxy)-N-[6-(1-methyl-piperidine-4-carbonyl)-pyridin-2-yl]-benzamide
57) 2-Chloro-N-[6-(1-methyl-piperidine-4-carbonyl)-pyridin-2-yl]-benzamide
58) 2,5-Difluoro-N-[6-(1-methyl-piperidine-4-carbonyl)-pyridin-2-yl]-benzamide
59) 3,4-Difluoro-N-[6-(1-methyl-piperidine-4-carbonyl)-pyridin-2-yl]-benzamide
60) 4-Fluoro-N-[6-(1-methyl-piperidine-4-carbonyl)-pyridin-2-yl]-2-trifluoromethyl-benzamide
61) 2-Fluoro-N-[6-(1-methyl-piperidine-4-carbonyl)-pyridin-2-yl]-6-trifluoromethyl-benzamide
62) 2,3,4-Trifluoro-N-[6-(1-methyl-piperidine-4-carbonyl)-pyridin-2-yl]-benzamide
63) 2,4,5-Trifluoro-N-[6-(1-methyl-piperidine-4-carbonyl)-pyridin-2-yl]-benzamide
64) 3-Chloro-thiophene-2-carboxylic acid [6-(1-methyl-piperidine-4-carbonyl)-pyridin-2-yl]-amide
65) 2,6-Dichloro-N-[6-(1-methyl-piperidine-4-carbonyl)-pyridin-2-yl]-benzamide
66) 2-Fluoro-N-[6-(1-methyl-piperidine-4-carbonyl)-pyridin-2-yl]-4-trifluoromethyl-benzamide
67) Cyclopentanecarboxylic acid [6-(1-methyl-piperidine-4-carbonyl)-pyridin-2-yl]-amide
69) N-[6-(1-Methyl-piperidine-4-carbonyl)-pyridin-2-yl]-nicotinamide It is preferred that the mammal to be treated by the administration of compounds of this invention is human.

The compounds of the present invention may be synthesized through a condensation of a 6-lithio anion of 2-chloro-pyridine with 1-substituted- or N-protected piperidine-4-carboxylic acid methoxy-methylamide, followed by conversion of the 2-halo group to an amino group, and subsequent condensation with the appropriate $R^1$-acylhalide compound. (see Scheme 1.)

Scheme 1:

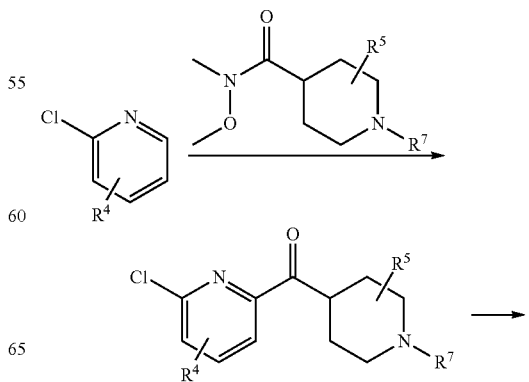

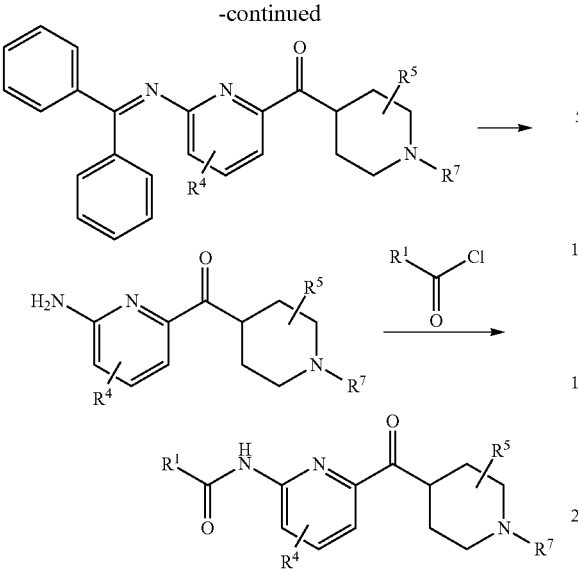

Suitable reaction conditions for the steps of this scheme are well known in the art and appropriate substitutions of solvents and reagents are within the skill of the art. See for example, J. C. S. Perkin T. (24), 3597-3600 (1997) for the initial condensation.

Typically 2-chloropyridine is activated by reaction with a mixture of n-butyl lithium and 2-dimethylamino-ethanol in a suitable solvent, such as hexane, at −78° C. The reaction is generally complete within about an hour. Next 1-$R^7$-substituted-piperidine-4-carboxylic acid methoxy-methyl-amide in an organic solvent, such as hexane is added and stirred to form the 2-chloropyridinoyl-piperidine intermediate. The reaction is generally complete within about an hour. When the desired final $R^2$ substituent is hydrogen, the piperidinyl nitrogen should first be protected with an amino protecting group, the addition and later removal of which are accomplished by standard procedures well known in the art.

Typically the first condensation reaction is quenched by the addition of water and the mixture is extracted multiple times with a suitable solvent, such as ethyl acetate. This 2-chloropyridinoyl-piperidine intermediate can then be dried, as for example with anhydrous sodium sulfate, evaporated, and then partially purified, as for example, by chromatography on a silica gel column.

Next, the 2-chloropyridinoyl-piperidine intermediate is reacted with benzophenone imine in the presence of tris(dibenzylidineacetone)-dipalladium(0) $Pd_2(dba)_3$) as a catalyst, and 2,2'-bis(diphenylphosphino)-1,1'binaphthyl (BINAP) and sodium t-butoxide in a suitable solvent, such as toluene, at reflux, to substitute the halo group with the benzophenone imino group. After work-up, this intermediate is typically reacted with hydrochloric acid in a suitable solvent, such as tetrahydrofuran, and then purified to give the corresponding 2-aminopyridinoyl-piperidine intermediate.

In the final stage of scheme I, the $R^1$ moiety is added by amide bond formation by reacting the 2-aminopyridinoyl-piperidine intermediate with the desired $R^1$-acylhalide. Typically, a mixture of the 2-aminopyridinoyl-piperidine intermediate, the desired $R^1$-acylhalide, a proton scavenger, such as triethylamine, diisopropylethylamine, and the like, in an appropriate solvent, such as dichloromethane, THF, MTBE and the like, is stirred at about room temperature until the reaction is complete, as for example, about 4 hrs. A strong base, such as sodium hydroxide, may then be added to neutralize the reaction mixture, and the final product purified by normal work-up procedures.

If the piperidinyl nitrogen is protected by an amino protecting group, this group is removed after the condensation reaction with the acylhalide. The piperidinyl nitrogen can then remain as a secondary amine for compounds of the present invention wherein $R^2$ is hydrogen, or it may be further alkylated by known procedures for compounds of the present invention wherein $R^2$ is $C_1$-$C_3$ alkyl, $C_3$-$C_6$ cycloalkyl-$C_1$-$C_3$ alkyl, or a group of formula II

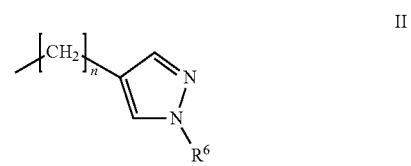

Although alternative alkylation methods are well known in the art, one typical alkylation reaction proceeds by reductive alkylation of the secondary amine with an appropriate aldehyde, an organic acid such as glacial acetic acid or trifluoroacetic acid, and a reducing agent such as sodium cyanoborohydride or sodium triacetoxyborohydride, in an appropriate solvent, such as methanol or dichloromethane, wherein the appropriate aldehyde is one that will react to provide the desired $R^2$ substituent. (Michael B. Smith and Jerry March, March's Advanced Organic Chemistry: Reactions, mechanisms and Structure, 5$^{th}$ ed., pgs 1185-1187 (sec. 16-12), John Wiley & Sons, Inc., New York, 2001.) By way of illustration, for the synthesis of compounds having $R^2$=methyl, the desired aldehyde would be formaldehyde, whereas for the synthesis of compounds having $R^2$=3-cyclopentylpropyl, the desired aldehyde would be 3-cyclopentylpropanal.

Compounds of the present invention wherein $R^3$ is methyl or ethyl can be synthesized by Scheme 2.

Scheme 2:

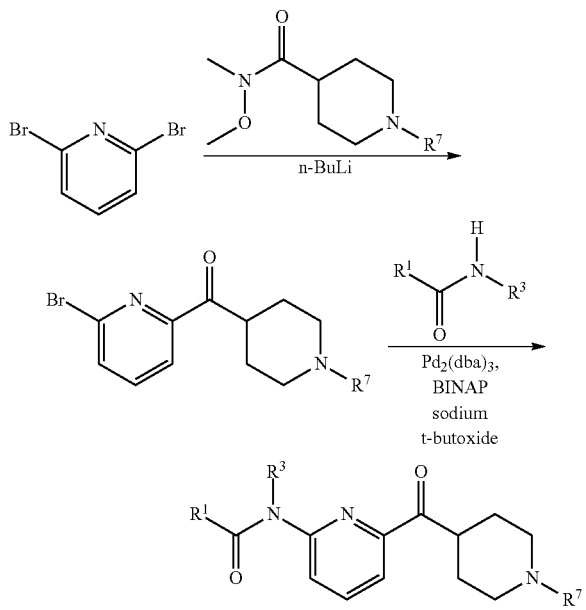

The $R^3$-aminocarbonyl-$R^1$ reagents are easily prepared by reacting the corresponding $R^1$ acylhalide with the desired amine (methylamine, ethylamine, propylamine, or isopropylamine, as for example a 2 M solution thereof) in an appropriate solvent, as for example methanol. Such a procedure is trivial and well known in the art.

The 2-bromopyridinoyl-piperidine intermediate is synthesized by first reacting 2,6-dibromopyridine in a suitable organic solvent, such as dichloromethane, preferably under a nitrogen atmosphere, with 1.1 equivalent of n-butyllithium in a suitable solvent, such as hexanes, preferably at low temperatures, such as −78° C. An appropriate 1-$R^7$-substituted-N-methoxy-N-methyl-piperidine-4-carboxamide is then Compounds of the present invention wherein $R^4$ or $R^5$ are other than hydrogen can be synthesized by the above schemes utilizing the corresponding substituted 2-halopyridine and substituted piperidinyl starting reagents.

In a preferred embodiment, a novel condensation reaction is used to synthesize the 2-bromopyridinoyl-piperidine intermediate to provide highly selective mono-addition, as well as higher yields of the desired intermediate product with fewer impurities. In another preferred embodiment, a more favorable reaction is used to convert the 2-bromopyridinoyl-piperidine intermediate to the 2-aminopyridinoyl-piperidine intermediate in preparation for the final condensation reaction. (See Scheme 3.)

Scheme 3:

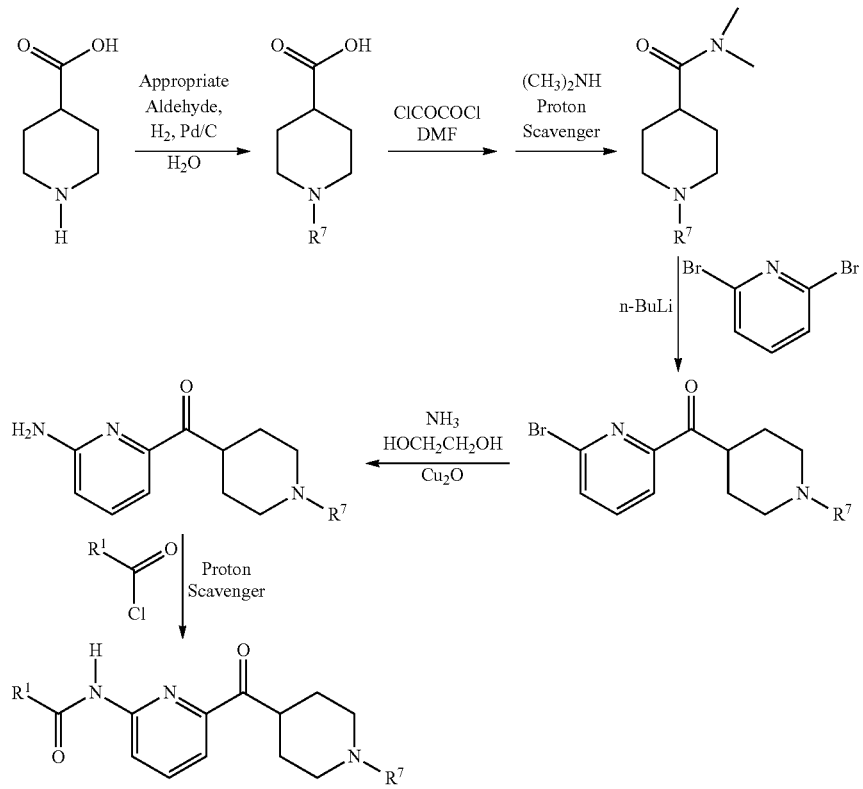

added to the reaction mixture. The reaction is subsequently quenched with base, as for example, aqueous NaOH. The resulting intermediate may then be purified by standard workup techniques, such as extraction, solvent removal and subsequent chromatography.

The 2-bromopyridinoyl-piperidine intermediate is reacted under $N_2$ in a mixture with the desired methylaminocarbonyl-$R^1$, ethylaminocarbonyl-$R^1$, or propylaminocarbonyl-$R^1$, respectively, tris(dibenzylidineacetone)-dipalladium(0) ($Pd_2(dba)_3$), 2,2'-bis(diphenylphosphino)-1,1'binaphthyl (BINAP), and sodium t-butoxide, in a suitable solvent, such as suitably anhydrous toluene. The reaction is typically heated for several hours, as for example at about 85° C. for 16 hours. Additional $C_1$-$C_2$ alkylaminocarbonyl-$R^1$, tris(dibenzylidineacetone)-dipalladium(0) ($Pd_2(dba)_3$), 2,2'-bis(diphenylphosphino)-1,1'binaphthyl (BINAP), and sodium t-butoxide can be added and the reaction continued for a similar period of time to improve the reaction yield. The final product is then purified by common methods.

The novel N,N-dimethylaminocarbonylpiperidine intermediate is made in high yield from an $R^7$-isonipicotic acid derivative by reacting the acid with oxalyl chloride in the presence of a catalytic amount of dimethylformamide (DMF) in a suitable solvent, such as dichloromethane, tetrahydrofuran, dichloroethane, diethylether, or the like, and concentrating to yield an isonipecotyl chloride derivative. This is then resuspended in a suitable solvent, such as tetrahydrofuran, dichloromethane, dichloroethane, diethylether, or the like, and reacted with dimethylamine in the presence of a proton scavenger, as for example, a non-nucleophilic organic base, such as triethylamine, diisopropylethylamine, or the like, and then purified to give the N,N-dimethylaminocarbonylpiperidine intermediate.

The N,N-dimethylcarbonylpiperidine intermediates of the present invention have the distinct advantages over the N-protected piperidine-4-carboxylic acid methoxy-methylamide reagents (Weinreb reagents) of the prior art, in that they are non-hygroscopic and surprisingly provide significantly improved chemoselectivity and yield in the subsequent condensation reaction as compared to the condensation reaction using the corresponding Weinreb reagent. This is particularly the case when, as in a preferred embodiment, toluene or methyl-tert-butylether (MTBE) is used as the solvent. In a yet more preferred embodiment, MTBE is used as the solvent.

Next, 2,6-dibromopyridine is activated by reaction with n-butyllithium in cold MTBE or toluene, preferably MTBE, to produce a bromolithiumpyridine intermediate. Subsequently, the N,N-dimethylaminocarbonylpiperidine intermediate is added and the mixture stirred, as for example for about an hour at between about −100° C. to about −60° C., preferably about −75° C. In a preferred embodiment, the coupling reaction is run with a ratio of the 2,6-dibromopyridine to the N,N-dimethylaminocarbonylpiperidine intermediate of about a 1.0 to about 2.0, more preferably with a ratio of between about 1.3 to about 1.7, most preferably with a ratio of about 1.5. The reaction is then quenched with saturated ammonium chloride at about −20° C. to about 10° C., and then neutralized with hydrochloric acid and additional water. The product can then be isolated by typical work-up procedures, as for example, but without limitation, by extraction of the aqueous phase with dichloromethane, washing the organic fractions with acidified water (as for example, pH 2), neutralizing the aqueous extract with sodium hydroxide, followed by extraction with ethyl acetate, drying the organic phase, as for example with magnesium sulfate, and concentrating, as for example, by evaporation, rotoevaporation, etc.

In another preferred embodiment, the 4-(N,N'-dimethylamino)carbonyl piperidine compound in Scheme 3 is replaced with a substituted aminocarbonylpiperidine compound of formula IV

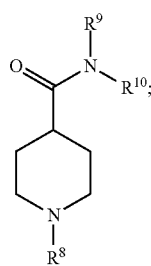

IV where $R^8$, $R^9$, and $R^{10}$ are as defined above. Preferred compounds of formula IV are those wherein $R^9$ and $R^{10}$ are each methyl, or wherein $R^9$ and $R^{10}$, together with the nitrogen to which they are attached, combine to form pyrrolidinyl. Particularly preferred are those compounds wherein $R^9$ and $R^{10}$, together with the nitrogen to which they are attached, combine to form pyrrolidinyl.

Compounds where $R^9$ and $R^{10}$, together with the nitrogen to which they are attached, combine to form azetidinyl, pyrrolidinyl, or piperidinyl, can be synthesized by the same methods as their N,N'-dimethyl analogs, by substituting azetidine, pyrrolidine, or piperidine, respectively, for the dimethylamine reagent described above.

The 4-(pyrrolidinylcarbonyl)piperidine reagents have the added advantage over the 4-(N,N'-dimethylamino)carbonyl piperidine reagents in that they tend to be even less hygroscopic and tend to produce more stable crystals, improving the handling characteristics of the reagents. As with the 4-(N,N'-dimethylamino)carbonyl piperidine reagents, the 4-(pyrrolidinylcarbonyl)piperidine reagents provide unexpected significantly improved chemoselectivity and yield in the subsequent condensation reaction over reactions run using the corresponding Weinreb reagents.

By way of illustration, but without limitation, 1-methyl-4-(N,N'-dimethylamino)carbonyl piperidine is a low melting point solid that crystallizes easily and has relatively low hygroscopicity, particularly as compared to the corresponding Weinreb reagent. However, when the crystalline form does absorb water, it converts to an oil. In comparison, 1-methyl-4-(pyrrolidinylcarbonyl)piperidine is also a low melting point solid that crystallizes easily, but is even less hygroscopic than 1-methyl-4-(N,N'-dimethylamino)carbonyl piperidine and produces more stable crystals, such that they retain their crystalline form even if some water is absorbed. 1-methyl-4-(piperidin-1-yl)carbonylpiperidine generally remains an oil.

In another embodiment of the present inventive process, 2,6-dichloropyridine can be used instead of 2,6-dibromopyridine in scheme 3, above under similar reaction conditions, to provide the corresponding 2-chloropyridinoylpiperidine intermediate.

In yet another preferred embodiment of the novel synthetic process, MTBE or toluene is used as the solvent, resulting in further improved chemoselectivity in the condensation reaction. MTBE as solvent is most preferred.

In a further embodiment of the present inventive process, the next step of the synthesis provides for the exchange of the halo group for an amino group by reaction of a 2-bromo-6-(piperidinylcarbonyl)pyridine intermediate, as described above, with ammonia and ethylene glycol, in the presence of copper(I) oxide as a catalyst. In a preferred embodiment, this reaction is run in an autoclave, with typical conditions being about 80° C. to about 110° C., preferably about 100° C., and from about 45 to about 60 psi (about 310 to about 414 kPa), typically about 50 psi (about 345 kPa). Ammonia is then removed from the organic fraction by evacuation. Aqueous sodium hydroxide is then added and the mixture extracted with a suitable organic solvent, as for example, methyl-tert-butylether or dichloromethane, and then dried, as for example, with magnesium sulfate.

In a preferred embodiment, the crude 2-amino-6-(1-$R^7$-piperidine-4-ylcarbonyl)pyridine intermediate is further purified by crystallization of the hydrochloric salt and then neutralizing the salt with sodium hydroxide, organic solvent extraction and solvent removal.

The final condensation reaction is as described in Scheme 1.

The following Preparations and Examples are illustrative and should not be interpreted in any way so as to limit the scope of the invention.

Preparations

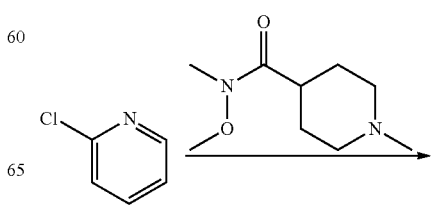

-continued

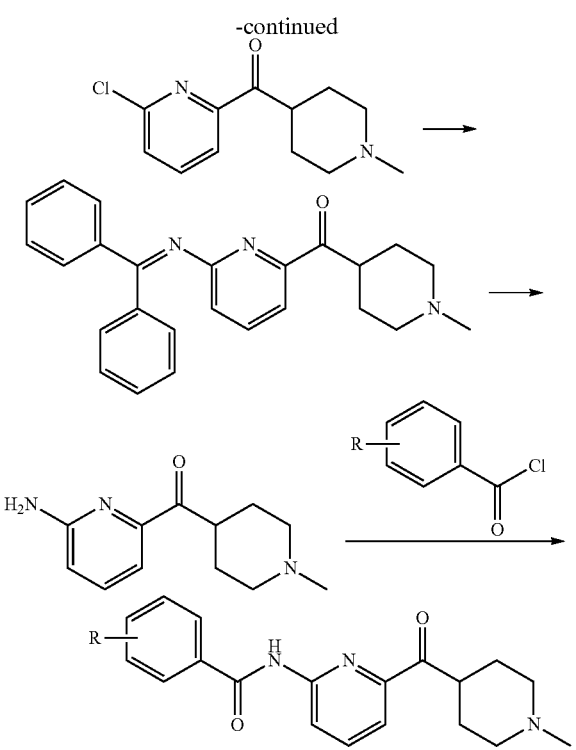

1. 2-Chloro-6-(1-methylpiperidin-4-ylcarbonyl)pyridine

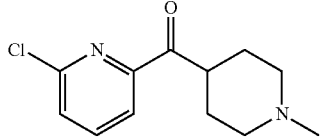 [SMILES: CN1CCC(C(=O)c2cccc(Cl)n2)CC1]

Add 2-chloropyridine (1 g, 8.8 mmole) to a mixture of n-butyl lithium (1.6 M in hexane) (22 mL, 35.2 mmole) and 2-dimethylamino-ethanol (1.56 g, 17.6 mmole) in hexane (20 mL at −78° C.) and stirred for 1 hour. Then add 1-methyl-piperidine-4-carboxylic acid methoxy-methyl-amide (3.2 g, 17.6 mmole) in hexane (5 mL) and stir the mixture for 1 hour. Quench the reaction mixture with water and extract twice with ethyl acetate, dry the organic layer with anhydrous sodium sulfate, evaporate the solvent and purify the residual product by chromatography on a silica gel column to give about 1 g of the title product.

2. 2-Amino-6-(1-methylpiperidin-4-ylcarbonyl)pyridine

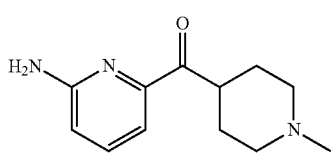 [SMILES: CN1CCC(C(=O)c2cccc(N)n2)CC1]

Heat a mixture of 2-chloro-6-(1-methylpiperidin-4-ylcarbonyl)pyridine (800 mg, 3.35 mmole), benzophenone imine (729 mg, 4.02 mmole), tris(dibenzylidineacetone)-dipalladium(0) (61 mg, 0.067 mmole), racemic-2,2'-bis(diphenylphosphino)-1,1'binaphthyl (83 mmole, 0.134 mmole) and sodium t-butoxide (451 mg, 4.69 mmole) in toluene (100 mL) at reflux for 2 hours. Evaporate the solvent and re-dissolve the residue in ethyl acetate, wash with water, dry with anhydrous sodium sulfate, evaporate and purify by chromatography on a silica gel column to give about 1 g of a benzophenone-imine intermediate. Add 1N HCl (12 mL) into a solution of the product in THF (50 mL), and stir at room temperature for 2 hours. Then add 25 mL of 1N HCl and extract the mixture twice with (2:1) hexane:ethyl acetate. Basify the aqueous phase, extract with dichloromethane, dry with anhydrous sodium sulfate, evaporate the solvent and purify the residual by chromatography on a silica gel column (ethyl acetate:2M NH₃ in methanol, 90:10) to give about 600 mg of the title product.

EXAMPLES 1. 4-Fluoro-N-[6-(1-methyl-piperidin-4-ylcarbonyl)-pyridin-2-yl]-benzamide dihydrochloride

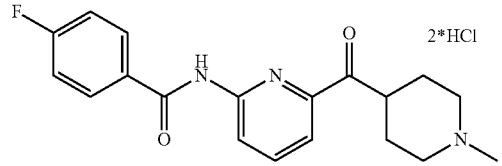 [SMILES: CN1CCC(C(=O)c2cccc(NC(=O)c3ccc(F)cc3)n2)CC1]

Stir a mixture of 2-Amino-6-(1-methylpiperidin-4-ylcarbonyl)pyridine (0.150 g), 4-fluorobenzoyl chloride (0.218 g), triethylamine (0.192 mL) and dichloromethane at room temperature for 4 hours. Add 1N aqueous NaOH to basify the reaction mixture. Extract the mixture with dichloromethane, dry the organic phase with anhydrous sodium sulfate, evaporate the solvent, and purify the residue by HPLC to provide the free base of the title compound. Re-dissolve the free base in diethyl ether and add excess 1 M HCl. Evaporate the solvent and dry the residue under vacuum to obtain 80 mg of the title compound. M.p. 75-80° C.; HRMS: 342.1605 (obs.) (Cal. 342.1618).

2. 2,4-Difluoro-N-[6-(1-methyl-piperidin-4-ylcarbonyl)-pyridin-2-yl]-benzamide dihydrochloride

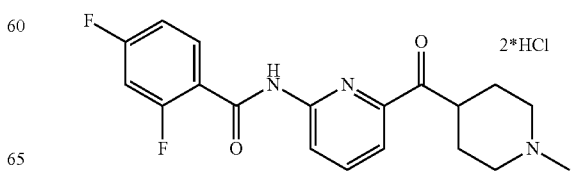

Use a method similar to the above example 1, with 2,4-difluorobenzoyl chloride to obtain the title compound. M.p. 108-110° C.; mass spectrum (electric spray) m/z=360.

3. 2-Chloro-4-fluoro-N-[6-(1-methyl-piperidin-4-ylcarbonyl)-pyridin-2-yl]-benzamide

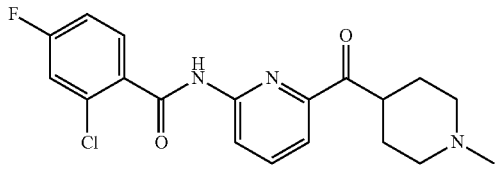 [SMILES: CN1CCC(C(=O)c2cccc(NC(=O)c3ccc(F)cc3Cl)n2)CC1]

Use a method similar to the above example 1, with 2-chloro-4-fluorobenzoyl chloride to obtain the title compound. Free base m.p. 53-55° C.; HRMS: 376.1233 (obs.) (Cal. 376.1228). Di-HCl salt m.p. 243-245° C.; HRMS: 376.1238 (obs.) (Cal. 376.1228).

4. 2-Chloro-6-fluoro-N-[6-(1-methyl-piperidin-4-ylcarbonyl)-pyridin-2-yl]-benzamide mono-hydrochloride salt

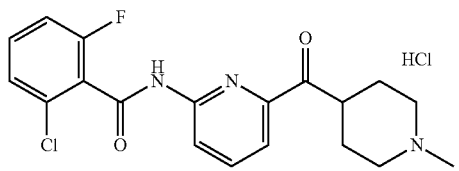 [SMILES: CN1CCC(C(=O)c2cccc(NC(=O)c3c(F)cccc3Cl)n2)CC1 ; Cl]

Combine 2-amino-6-(1-methylpiperidin-4-ylcarbonyl)pyridine (0.18 g, 0.85 mmol), 2-chloro-6-fluoro-benzoyl chloride (0.318 g, 1.65 mmol), and 1,4-dioxane (10 mL). Stir and heat the mixture at reflux. After 2 hr., cool the reaction mixture to ambient temperature and concentrate. Load the mixture onto an SCX column (10 g), wash with methanol, and elute with 2M ammonia/methanol. Concentrate the eluent to obtain the free base of the title compound (0.30 g, 94%) as an oil. Dissolve the oil in methanol (5 mL) and treat with ammonium chloride (0.045 g, 0.85 mmol). Concentrate the mixture and dry under vacuum to obtain the title compound. HRMS Obs. m/z 376.1237; Calc. m/z 376.1228; m.p. 155° C. (dec).

5. 2-Bromo-N-[6-(1-methyl-piperidin-4-ylcarbonyl)-pyridine-2-yl]benzamide hydrochloride salt

Use a method similar to example 1, with 2-bromobenzoyl chloride to obtain the free base of the title compound. Dissolve the clean material (104.8 mg) in methanol and add 1 equivalent (13.9 mg) of NH₄Cl. Sonicate the reaction mixture at room temperature for 15 min. and then concentrate and dry the mixture to provide the title compound as a white solid. Mass spectrum (ion spray): m/z=402.1 (M+1); $^1$H NMR δ (d6-DMSO, ppm) 11.15 (1H, s), 8.37 (1H, bs), 8.07 (1H, t, J=7.69, 8.05, 15.74 Hz), 7.74 (2H, m), 7.58 (3H, m), 3.70 (1H, bs), 2.87 (2H, m), 2.65 (3H, s), 2.12 (3H, m), 1.82 (3H, m)

6. 2-Chloro-N-[6-(1-methyl-piperidin-4-ylcarbonyl)-pyridin-2-yl]-benzamide

Mix 2-Amino-6-(1-methylpiperidin-4-ylcarbonyl)pyridine (0.223 g) and 2-chlorobenzoyl chloride (0.175 g) in 1,4-dioxane (10 mL) and heat at reflux for 1 hour. Dilute with methanol (10 mL) and load on a SCX column (10 g). Wash the column with methanol, elute the product with 2 M NH₃ in methanol, evaporate and purify the product on a silica gel column (CH₂Cl₂ with 2 M NH₃ in methanol) to obtain 0.305 g (84%) of the title compound: mass spectrum (electric spray) m/z=358 (M+1) and 360 (M+2+1); $^1$H NMR (CDCl₃): 8.60 (br s, 1H), 8.54 (d, 1H), 7.90 (dd, 1H), 7.81 (d, 1H), 7.76 (dd, 1H), 7.45 (m, 3H), 3.63 (m, 1H), 2.90 (m, 2H), 2.29 (s, 3H), 2.07 (m 2H), 1.85 (m, 4H).

Dissolve the free base in dichloromethane and add 1N HCl in ether (0.85 mL), evaporate, and dry under vacuum to obtain the monohydrochloride salt (0.354 g).

7. N-[6-(1-Methyl-piperidin-4-ylcarbonyl)-pyridin-2-yl]-benzamide hydrochloride

Use a method similar to the above example 1, with benzoyl chloride to obtain the free base of the title compound. Re-dissolve the free base in diethyl ether and add 1 M HCl in a 1:1 molar ratio. Evaporate the solvent and dry the residue under vacuum to obtain the title compound. HRMS: 324.1697 (obs.) (Cal. 324.1712).

8. 2,4,6-Trifluoro-N-[6-(1-methyl-piperidin-4-ylcarbonyl)-pyridin-2-yl]-benzamide mono-hydrochloride salt

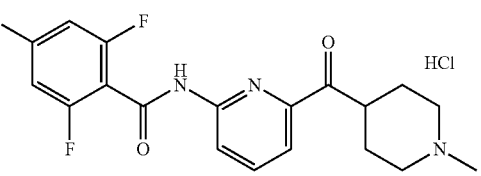

Combine 2-amino-6-(1-methylpiperidin-4-ylcarbonyl)pyridine (0.20 g, 0.92 mmol), 2,4,6-Trifluorobenzoyl chloride (0.357 g, 1.84 mmol), and 1,4-Dioxane (10 mL), and stir while heating at reflux. After 3 hr., cool the reaction mixture to ambient temperature and concentrate. Load the concentrated mixture onto an SCX column (10 g), wash with methanol, and elute with 2M ammonia in methanol. Concentrate the eluent to obtain the free base of the title compound as an oil (0.365 g (>100%)). Dissolve the oil in methanol (5 mL) and treat with ammonium chloride (0.05 g, 0.92 mmol). Concentrate the mixture and dry under vacuum to obtain the title compound. HRMS Obs. m/z 378.1435, Calc. m/z 378.1429; m.p. 255° C. (dec).

9. 2-Trifluoromethyl-4-fluoro-N-[6-(1-methyl-piperidin-4-ylcarbonyl)-pyridin-2-yl]-benzamide monohydrochloride salt

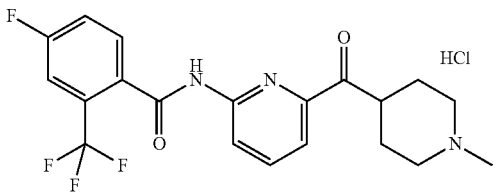 [SMILES: CN1CCC(C(=O)c2cccc(NC(=O)c3ccc(F)cc3C(F)(F)F)n2)CC1 ; Cl]

Combine 2-amino-6-(1-methylpiperidin-4-ylcarbonyl)pyridine (0.19 g, 0.87 mmol), 2-trifluoromethyl-4-fluoro-benzoyl chloride (0.395 g, 1.74 mmol), and 1,4-Dioxane (50 mL). Stir and heat the mixture at reflux. After 3 hr., cool the reaction mixture to ambient temperature and concentrate. Load the mixture onto an SCX column (10 g), wash with methanol, and elute with 2M ammonia/methanol. Concentrate the eluent to obtain the free base of the title compound as an oil (0.241 g, 68%). Dissolve the oil in methanol (5 mL) and treat with ammonium chloride (0.031 g, 0.59 mmol). Concentrate and dry under vacuum to obtain the title compound. HRMS Obs. m/z 410.1490, Calc. 410.1491; m.p. 145-150° C.

10. 2-Trifluoromethoxy-N-[6-(1-methyl-piperidin-4-ylcarbonyl)-pyridin-2-yl]-benzamide mono-hydrochloride salt

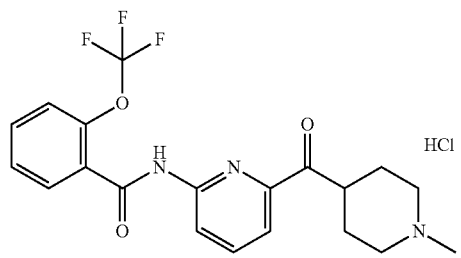 [SMILES: CN1CCC(C(=O)c2cccc(NC(=O)c3ccccc3OC(F)(F)F)n2)CC1 ; Cl]

Combine 2-amino-6-(1-methylpiperidin-4-ylcarbonyl)pyridine (0.18 g, 0.84 mmol), 2-trifluoromethoxybenzoyl chloride (0.23 g, 1.0 mmol) and 1,4-Dioxane (5 mL). Stir and heat the mixture at reflux. After 3 hr., cool the reaction mixture to ambient temperature. Load on an SCX column (10 g), wash with methanol, and elute with 2M ammonia/methanol. Concentrate the eluent to obtain the free base of the title compound (0.26 g, 76%). Dissolve the free base in methanol (10 mL) and treat with ammonium chloride (0.032 g). Concentrate and dry under vacuum to obtain the title compound. HRMS Obs. m/z 408.1517, Calc. m/z 408.1535; m.p. 155-160° C.

11. 3-Bromo-N-[6-(1-methyl-piperidin-4-ylcarbonyl)-pyridin-2-yl]-thiophene-2-carboxamide monohydrochloride salt

Combine 2-amino-6-(1-methylpiperidin-4-ylcarbonyl)pyridine (0.104 g, 0.48 mmol), 3-Bromo-thiophene-2-carbonyl chloride (0.215 g, 0.95 mmol), and 1,4-Dioxane (10 mL). Stir and heat the mixture at reflux. After 2 hr., cool the reaction mixture to ambient temperature and concentrate. Load the mixture onto an SCX column (10 g), wash with methanol, and elute with 2M ammonia/methanol. Concentrate the eluent to obtain the free base of the title compound as an oil (0.152 g, 78%). Dissolve the oil in dichloromethane (10 mL), treat with 1M hydrogen chloride in ether, concentrate and dry under vacuum to obtain the title compound. HRMS Obs. m/z 408.0384, Calc. m/z 408.0381; m.p. 195-200° C.

12. 1-H-indol-3-yl-N-[6-(1-methylpiperidin-4-ylcarbonyl)-pyridin-2-yl]-carboxamide dihydrochloride salt

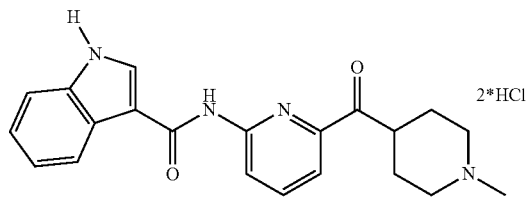

(i) Intermediate: 1-Benzylindol-3-yl-N-[6-(1-methylpiperidin-4-ylcarbonyl)-pyridin-2-yl]-carboxamide

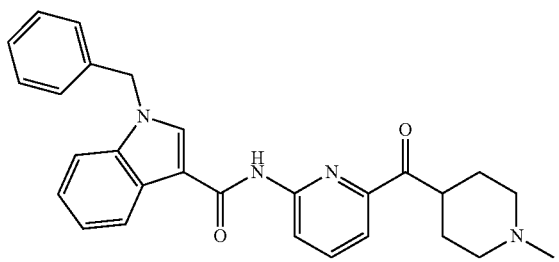 [SMILES: CN1CCC(C(=O)c2cccc(NC(=O)c3cn(Cc4ccccc4)c4ccccc34)n2)CC1]

Add oxalyl chloride (0.18 mL, 2.1 mmol) dropwise to a solution of 1-benzylindol-3-carboxylic acid (0.48 g, 1.9 mmol) in pyridine and CH₃CN (5 mL each) cooled in an ice bath. Stir the reaction mixture for 2.25 hr. and then add a suspension of 2-amino-6-(1-methylpiperidin-4-ylcarbonyl)

pyridine (0.56 g, 1.9 mmol) in CH₃CN (5 mL) and pyridine (12 mL). Warm the reaction mixture to room temperature overnight. Quench the reaction with cold H$_2$O (20 mL) and dilute with CHCl$_3$. Adjust the pH to 11 with Na$_2$CO$_3$ and separate the layers. Extract the aqueous layer with CHCl$_3$ (2×30 mL). Combine the organic fractions and dry with anhydrous MgSO$_4$, filter and concentrate the mixture in vacuo. Purify the product by chromatography on a silica gel column, eluting with methanol/CH$_2$Cl$_2$ (5:95) followed by methanol/CH$_2$Cl$_2$ (10:90) to afford the sub-title compound (0.44 g, 51%). $^1$H NMR (CD$_3$OD) δ 8.45 (d, J=8 Hz, 1H), 8.32 (s, 1H), 8.26 (m, 1H), 7.95 (t, J=8 Hz, 1H), 7.72 (d, J=8 Hz, 1H), 7.45 (m, 1H), 7.22-7.37 (m, 7H), 5.51 (s, 2H), 3.90 (m, 1H), 2.93-3.01 (m, 2H), 2.33 (s, 3H), 2.21-2.31 (m, 2H), 1.92-1.99 (m, 2H), 1.71-1.84 (m, 2H); CIMS (Methane) m/z 453 [C$_{28}$H$_{28}$N$_4$O$_2$+H]$^+$.

(ii) 1H-indol-3-yl-N-[6-(1-methylpiperidin-4-ylcarbonyl)-pyridin-2-yl]-carboxamide

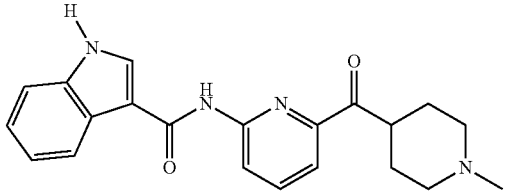 [SMILES: CN1CCC(C(=O)c2cccc(NC(=O)c3c[nH]c4ccccc34)n2)CC1]

Add aluminum trichloride (106 mg, 0.795 mmol) to a suspension of 1-benzylindol-3-yl-N-[6-(1-methylpiperidin-4-ylcarbonyl)-pyridin-2-yl]-carboxamide (180 mg, 0.398 mmol) in benzene (6 mL) and heat the mixture at reflux for 1.25 hr. Then add another 2 equivalents of aluminum trichloride (108 mg) and continue heating at reflux for an additional 5.5 hr. Cool the reaction mixture to room temperature. Then pour the reaction into ice cold H$_2$O (50 mL) and then dilute with ethyl acetate. Adjusted the pH of the solution to 11 with saturated Na$_2$CO$_3$, separate the layers and extract the aqueous layer with ethyl acetate (3×50 mL). Combined the organic fractions, dry with Na$_2$SO$_4$, filter and concentrate in vacuo. Purify the intermediate by flash chromatography on a silica gel column, eluting with CHCl$_3$/methanol/NH$_4$OH (93:7:1) to obtain the sub-title compound (96 mg, 67%). $^1$H NMR (CD$_3$OD) δ 8.45 (d, J=8 Hz, 1H), 8.25 (s, 1H), 8.21 (m, 1H), 7.96 (t, J=8 Hz, 1H), 7.72 (d, J=8 Hz, 1H), 7.48 (m, 1H), 7.18-7.27 (m, 2H), 3.90 (m, 1H), 2.94-3.01 (m, 2H), 2.31 (s, 3H), 2.19-2.28 (m, 2H), 1.92-2.02 (m, 2H), 1.71-1.84 (m, 2H). CIMS (Methane) m/z 363 [C$_{21}$H$_{22}$N$_4$O$_2$]$^+$.

(iii) 1-H-indol-3-yl-N-[6-(1-methylpiperidin-4-ylcarbonyl)-pyridin-2-yl]-carboxamide dihydrochloride salt

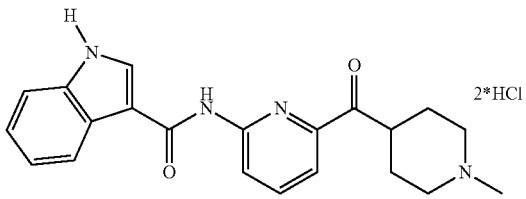

Add 2.0M HCl in diethylether (0.46 mL, 0.93 mmol) to a suspension of 1H-indol-3-yl-N-[6-(1-methylpiperidin-4-ylcarbonyl)-pyridin-2-yl]-carboxamide (free base) (0.16 g, 0.44 mmol) in diethylether (10 mL). After 2 hr. filter the reaction mixture and wash the solid with diethylether to afford the title compound as a yellow solid. R$_f$ 0.29 (93:7:1 CHCl$_3$/methanol/NH$_4$OH); m.p. 200-218° C.; $^1$H NMR (CD$_3$OD, complex mixture of rotamers) δ 8.38 and 8.49 (s, 1H), 8.46 (m, 1H), 8.08-8.10 and 8.18-8.29 (m, 2H), 7.61 and 7.72 (d, J=8 Hz, 1H), 7.52 (m, 1H), 7.26-7.32 (m, 2H), 4.01 (m, 1H), 3.19-3.68 (m, 3H), 2.97 (m, 1H), 2.82 and 2.94 (s, 3H), 2.28-2.32 (m, 2H), 1.68-2.02 (m, 2H); CIMS (Methane) m/z 363 [C$_{21}$H$_{22}$N$_4$O$_2$+H]$^+$; HPLC (Method A) 96.7%, t$_R$ 16.4 min.; anal. calculated for C$_{21}$H$_{22}$N$_4$O$_2$.2.1HCl.1.5H$_2$O: C, 54.12; H, 5.86; N, 12.02; Cl, 15.98. Found: C, 54.13; H, 6.03; N, 12.37; Cl, 15.71.

13. Cyclopropyl-[6-(1-methylpiperidin-4-ylcarbonyl)-pyridin-2-yl]-carboxamide dihydrochloride salt

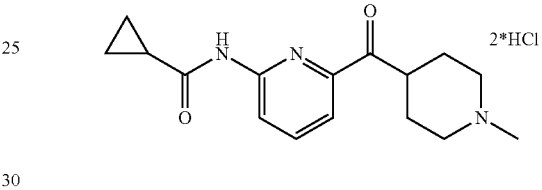

Add cyclopropylcarbonyl chloride (0.08 mL, 0.83 mmol) dropwise to a solution of 2-amino(6-pyridyl)-1-methyl(4-piperidyl)-ketone (221 mg, 0.76 mmol) and triethylamine (0.32 mL, 2.3 mmol) in CH$_2$Cl$_2$ (5 mL) cooled in an ice bath. Warm the reaction mixture to room temperature and stir for 3 hr. Extract the reaction mixture with CH$_2$Cl$_2$ and H$_2$O and adjust the pH of the aqueous layer to 11 with Na$_2$CO$_3$. Separate the layers and extract the aqueous layer with CH$_2$Cl$_2$ (2×50 mL). Combine the organic fractions, dry (Na$_2$SO$_4$), filter and concentrate in vacuo. Purify the concentrate by chromatography on a silica gel column, eluting with a gradient of CH$_2$Cl$_2$/methanol (95:5 to 90:10) to obtain the free base of the title compound (180 mg, 83%). $^1$H NMR (CDCl$_3$, complex mixture of rotamers.) δ 8.81 (bs, 1H), 8.39 (d, J=8 Hz, 1H), 7.82 (t, J=8 Hz, 1H), 7.71 (d, J=8 Hz, 1H), 3.50 (m, 1H), 3.13-3.21 (m, 2H), 2.51 (s, 3H), 2.37-2.48 (m, 4H), 1.95-2.04 (m, 2H), 1.55 and 1.82 (m, 1H), 0.75-0.81, 0.90-0.99 and 1.10-1.14 (m, 4H); APCI MS m/z 288 [C$_{16}$H$_{21}$N$_3$O$_2$+H]$^+$.

Add 2.0M HCl in diethyl ether (0.95 mL, 1.9 mmol) to a solution of the free base (180 mg, 0.626 mmol) in diethyl ether (10 mL) and methanol (3 mL). After 2 hr. the reaction was filtered to afford the title compound as a light yellow solid. R$_f$ 0.47 (93:7:1 CHCl$_3$/methanol/NH$_4$OH); m.p. 140-148° C.; $^1$H NMR (CD$_3$OD, complex mixture of rotamers) δ 8.24 and 8.50 (m, 1H), 8.05-8.08 (m, 1H), 7.52 and 7.64 (d, J=8.0 Hz, 1H), 3.98 and 4.16 (m, 1H), 3.62-3.66 (m, 1H), 3.20-3.28 and 3.44-3.56 (m, 2H), 2.91-3.04 (m, 1H), 2.80 and 2.93 (s, 3H), 2.13-2.29 (m, 2H), 1.57-1.79 and 1.92-2.06 (m, 3H), 1.01-1.21 (m, 4H); CIMS (Methane) m/z 288 [C$_{16}$H$_{21}$N$_3$O$_2$+H]$^+$; HPLC>99%, t$_R$ 14.9 min.; anal. calcu-

14. 2-Methylprop-1-yl-N-[6-(1-methylpiperidin-4-ylcarbonyl)-pyridin-2-yl]-carboxamide dihydrochloride salt

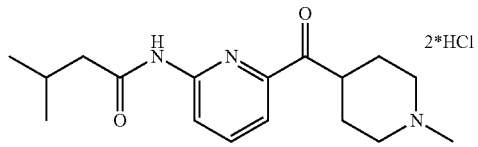

(i) Free Base:

Add 3-methylbutanoyl chloride (0.11 mL, 0.90 mmol) dropwise to a solution of 2-amino-6-(1-methylpiperidin-4-ylcarbonyl)pyridine (132 mg, 0.45 mmol) and triethylamine (0.19 mL, 1.4 mmol) in $CH_2Cl_2$ (5 mL) cooled in an ice bath. Warm the reaction mixture to room temperature and stir for 3 hr. Dilute the reaction with $CH_2Cl_2$ and wash with saturated $NaHCO_3$ (50 mL). Extract the aqueous layer with $CH_2Cl_2$ (2×25 mL). Combine the organic fractions, dry ($Na_2SO_4$), filter and concentrate in vacuo. Purify the product by chromatography on a silica gel column, eluting with $CH_2Cl_2$/methanol (95:5) to obtain the free base of the title compound (88 mg, 64%). $^1$H NMR ($CDCl_3$) δ 8.44 (d, J=8.0 Hz, 1H), 7.81-7.86 (m, 1H), 7.73 (d, J=7.1 Hz, 1H), 3.50 (m, 1H), 3.00-3.18 (m, 2H), 2.18-2.46 (m, 7H), 1.92-2.01 (m, 2H), 1.52-1.71 (m, 3H), 1.05 (d, J=6.6 Hz, 6H); CIMS (Methane) m/z 304 $[C_{17}H_{25}N_3O_2+H]^+$.

(ii) Dihydrochloride Salt:

Add 2.0M HCl in diethyl ether (0.36 mL, 0.73 mmol) to a solution of the free base (88 mg, 0.29 mmol) in diethyl ether (5 mL) and methanol (2 mL). After 2 hr., concentrate the reaction mixture in vacuo to obtain the title compound as a brown solid. $R_f$ 0.58 (93:7:1 $CHCl_3$/methanol/$NH_4OH$); m.p. 93-95° C.; $^1$H NMR ($CD_3OD$, complex mixture of rotamers) δ 8.35 (m, 1H), 7.95 (m, 1H), 7.77 (m, 1H), 4.06 and 4.25 (m, 1H), 3.43-3.52 and 3.61-3.65 (m, 2H), 3.18-3.28 (m, 2H), 2.81-2.94 (m, 3H), 2.21-2.37 (m, 5H), 1.90-2.02 (m, 2H), 1.03-1.05 (m, 6H); CIMS (Methane) m/z 304 $[C_{17}H_{25}N_3O_2+H]^+$; HPLC 98.4%, Symmetry® series C18 column, Waters Corporation, Milford, Mass. (4.6×250 mm); anal. calculated for $C_{17}H_{25}N_3O_2 \cdot 1.9HCl \cdot 1.2H_2O$: C, 51.79; H, 7.49; N, 10.66; Cl, 17.08. found: C, 51.78; H, 7.64; N, 10.35; Cl, 17.07.

15. 2,4,6-Trifluoro-N-methyl-N-[6-(1-methyl-piperidin-4-ylcarbonyl)-pyridin-2-yl]-benzamide hydrochloride salt

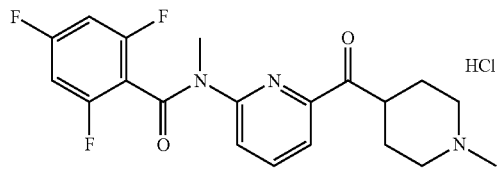 [SMILES: CN1CCC(C(=O)c2cccc(N(C)C(=O)c3c(F)cc(F)cc3F)n2)CC1 ; Cl]

Dissolve 2,6-dibromopyridine (3.6 g, 15.3 mmol) in anhydrous dichloromethane (90 mL) under nitrogen atmosphere. Cool the reaction mixture to −78° C. Add a solution of n-butyl lithium in hexane very slowly via a syringe (1.6 M, 10.5 mL, 16.9 mmol). After the addition is complete, stir the reaction at −78° C. for 1 hr. Add a solution of 4-(methoxy-methyl-aminocarbonyl)-piperidine-1-carboxylic acid tert-butyl ester (2 g, 7.3 mmol) in anhydrous dichloromethane (10 mL) dropwise to the reaction mixture. Stir the reaction at −78° C. for 2 hrs., then allow it to slowly warm to room temperature overnight. Quench the reaction with 0.1 N aqueous NaOH. Dilute the solution with dichloromethane (100 mL), transfer into a separation funnel and shake with 0.1 N NaOH (60 mL). Separate the organic layer and dry it over anhydrous sodium sulfate. Evaporate the solvent under reduced pressure. Further purify the residue by chromatography on silica gel column (10%-30% ethyl acetate/hexane) to obtain 2-bromo-6-(1-t-butoxycarbonylpiperidin-4-ylcarbonyl)-pyridine (2.7 g, quantitative yield). Mass spectrum (ion spray): m/z 370 (M+1).

Heat a mixture of 2-bromo-6-(1-t-butoxycarbonylpiperidin-4-ylcarbonyl)-pyridine (152 mg, 0.41 mmol), N-methyl-2,4,6-trifluorobenzamide (92.6 mg, 0.49 mmol), $Pd_2(dba)_3$ (9.2 mg, 0.01 mmol), BINAP (12.4 mg, 0.02 mmol), sodium t-butoxide (55 mg, 0.57 mmol) in anhydrous toluene (10 mL) at 85° C. for 16 hrs. Cool the reaction to room temperature and add another aliquot of N-methyl-2,4,6-trifluorobenzamide, $Pd_2(dba)_3$, BINAP and sodium t-butoxide in the same amount. Re-heat the reaction at 85° C. for 16 more hours. Extract the reaction mixture with ethyl acetate and aqueous NaOH (0.1N). Collect and dry the organic layers. Concentrate and purify the crude product by chromatography (silica gel, 10%-30% ethyl acetate/hexane) to obtain 2,4,6-trifluoro-N-methyl-N-[6-(1-t-butoxycarbonyl-piperidin-4-ylcarbonyl)-pyridin-2-yl]-benzamide (86 mg, 44% yield).

Dissolve the 2,4,6-trifluoro-N-methyl-N-[6-(1-t-butoxycarbonyl-piperidin-4-ylcarbonyl)-pyridin-2-yl]-benzamide in 50% trifluoroacetic acid/$CH_2Cl_2$ (24 mL) and stir for 45 min. Remove volatiles under reduced pressure and extract with ethyl acetate and aqueous NaOH (2M). Combine the organic layers and dry with sodium sulfate. Concentrate and purify the residue by chromatography (silica gel/6% of (2M $NH_3$ in methanol)/$CH_2Cl_2$) to afford 2,4,6-trifluoro-N-methyl-N-[6-(piperidin-4-ylcarbonyl)-pyridin-2-yl]-benzamide (77 mg, 85% yield).

Dissolve the 2,4,6-trifluoro-N-methyl-N-[6-(piperidin-4-ylcarbonyl)-pyridin-2-yl]-benzamide (77 mg, 0.20 mmol) in methanol (10 mL), add 37% aqueous formaldehyde (0.16 mL, 2.0 mmol), glacial acetic acid (0.34 mL, 6.0 mmol) and $NaBH_3CN$ (21.9 mg, 0.35 mmol). Stir the reaction mixture at room temperature. Extract the mixture with ethyl acetate and aqueous NaOH (2M) to obtain 2,4,6-trifluoro-N-methyl-N-[6-(α-hydroxy-(1-methylpiperidin-4-ylcarbonyl)-methyl)-pyridin-2-yl]-benzamide. Dissolve the 2,4,6-trifluoro-N-methyl-N-[6-(α-hydroxy-(1-methylpiperidin-4-ylcarbonyl)-methyl)-pyridin-2-yl]-benzamide in anhydrous $CH_2Cl_2$ (12 mL) and treat under $N_2$ with Dess-Martin reagent (127 mg, 0.30 mmol) for 1 hr. Extract with ethyl acetate and 2M aqueous NaOH. Collect and dry the organic layers. Concentrate and purify the residue by chromatography (silica gel/6% of (2M $NH_3$ in methanol)/$CH_2Cl_2$) to afford the free amine of the title compound (60.2 mg, 77% yield). Dissolve the free base in methanol (10 mL) and treat with ammonium chloride (0.032 g). Concentrate and dry under vacuum to obtain the title compound. Mass spectrum (ion spray): m/z=392.0 (M+1); $^1$H NMR (methanol-$d_4$): 7.85 (m, 2H), 7.50 (m, 1H), 6.80 (m, 2H), 3.75 (m, 1H), 3.52 (d, 2H), 3.47 (s, 3H), 3.20 (t, 2H), 2.94 (s, 3H), 2.03 (d, 2H), 1.83 (m, 2H).

16. 2,4,6-Trifluoro-N-ethyl-N-[6-(1-methyl-piperidin-4-ylcarbonyl)-pyridin-2-yl]-benzamide hydrochloride salt

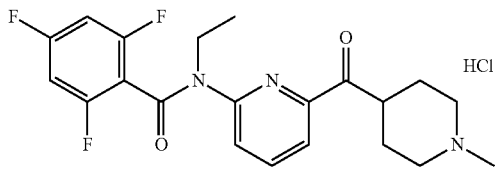 [SMILES: CCN(C(=O)c1c(F)cc(F)cc1F)c1cccc(C(=O)C2CCN(C)CC2)n1 ; Cl]

Dissolve 2,6-dibromopyridine (5.5 g, 23.2 mmol) in anhydrous dichloromethane (140 mL) under a nitrogen atmosphere. Cool the reaction mixture to −78° C. Add a solution of n-butyl lithium in hexane (1.6 M, 15.8 mL, 25.3 mmol) very slowly via a syringe. After the addition is complete, stir the reaction at −78° C. for 1 hr. Add a solution of 1-methyl-N-methyl-N-methoxy-piperidine-4-carboxamide (2 g, 11 mmol) in anhydrous dichloromethane (10 mL) dropwise to the reaction mixture. Stir the reaction at −78° C. for 2 hrs, and then allow the mixture to slowly warm to room temperature overnight. Quench the reaction with 0.1 N NaOH. Dilute the solution with dichloromethane (100 mL), transfer into a separatory funnel and shake with 2 N NaOH (50 mL). Separate the organic layer, dry it over anhydrous sodium sulfate, and then evaporate the solvent under reduced pressure. Further purify the residue by chromatography on asilica gel column (6%, 2M NH$_3$ in methanol/CH$_2$Cl$_2$) to obtain 2-bromo-6-(1-methylpiperidin-4-ylcarbonyl)-pyridine (2.3 g, 74% yield). Mass spectrum (ion spray): m/z 283 (M+1).

Combine 2-bromo-6-(1-methylpiperidin-4-ylcarbonyl)-pyridin (189 mg, 0.67 mmol), N-ethyl-2,4,6-trifluorobenzamide (162 mg, 0.80 mmol), Pd$_2$(dba)$_3$ (14.6 mg, 0.016 mmol), BINAP (19.9 mg, 0.032 mmol), sodium t-butoxide (90.2 mg, 0.94 mmol) and anhydrous toluene (10 mL), and heat the mixture at 85° C. for 16 hr. under a nitrogen atmosphere. Cool the reaction to room temperature and add additional N-ethyl-2,4,6-trifluorobenzamide, Pd$_2$(dba)$_3$, BINAP, sodium t-butoxide in the same amounts. Re-heat the reaction at 85° C. for 16 more hours. Extract with ethyl acetate and aqueous NaOH (0.1N). Collect and dry the organic layers. Concentrate and purify the residue by chromatography (silica gel, 10%-30% ethyl acetate/hexanes) to obtain the free base of the title compound (100 mg, 37% yield). Dissolve the free base in methanol (10 mL) and treat with ammonium chloride (0.032 g). Concentrate and dry under vacuum to obtain the title compound. Mass spectrum (ion spray): m/z=406.1 (M+1); $^1$H NMR (methanol-$d_4$): 7.94 (m, 2H), 7.54 (m, 1H), 6.88 (m, 2H), 4.12 (q, 2H), 3.86 (m, 1H), 3.77 (d, 2H), 3.18 (t, 2H), 2.94 (s, 3H), 2.15 (d, 2H), 1.92 (m, 2H).

17. 2,4,6-Trifluoro-N-[6-(piperidin-4-ylcarbonyl)-pyridin-2-yl]-benzamide

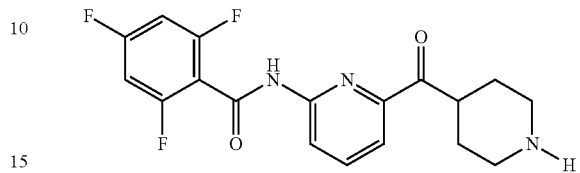

Add 1-chloroethyl chloroformate (0.8 g) into a solution of 2,4,6-trifluoro-N-[6-(1-methyl-piperidin-4-ylcarbonyl)-pyridin-2-yl]-benzamide (0.216 g) in dichloroethane (10 mL) and heat at reflux for 1 hr. Then add more 1-chloroethyl chloroformate (1 mL) and heat at reflux overnight. Add methanol (10 mL) to the reaction mixture, concentrate to a small volume, dilute with methanol again, load onto an SCX column (10 g), wash with methanol, and elute with 2M NH$_3$-methanol, evaporate and purify on a silica gel column (CH$_2$Cl$_2$ with 2 M NH$_3$ in methanol) to obtain the title compound (61 mg). Mass spectrum (electric spray) m/z=364 (M+1); $^1$H NMR (CDCl$_3$): 8.55 (d, J=8.1 Hz, 1H), 7.92 (dd, J=8.0, 8.0 Hz 1H), 7.84 (1H, J=8.0 Hz, 1H), 6.81 (m, 3H), 3.89 (m, 1H), 3.12 (br d, 2H), 2.81 (m, 2H), 1.85 (m, 2H), 1.74 (br, 2H), 1.61 (m, 2H).

Add 0.17 mL of 1N HCl in ether into a solution of the free base in methylene chloride-methanol, evaporate the solvent and dry under vacuum to obtain the monohydrochloride salt.

18. 2,4,6-Trifluoro-N-[6-(1-ethylpiperidin-4-ylcarbonyl)-pyridin-2-yl]-benzamide

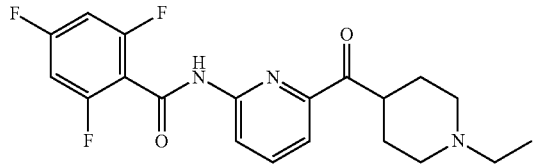 [SMILES: CCN1CCC(C(=O)c2cccc(NC(=O)c3c(F)cc(F)cc3F)n2)CC1]

Mix 2,4,6-trifluoro-N-[6-(piperidin-4-ylcarbonyl)-pyridin-2-yl]-benzamide (26 mg), acetaldehyde (42 mg), sodium cyanoborohydride (10 mg) and trifluoroacetic acid (16.4 mg) in methanol (2 mL) in a sealed tube and heat in an oil bath at 90° C. overnight. Dilute with methanol and load on a SCX column (10 g), wash with methanol, elute the product with 2M NH$_3$-methanol, evaporate, purify on a silica gel column (4 g, solvent: dichloromethane-2M NH$_3$ in methanol, gradient) to obtain the title compound (8.4 mg). Mass spectrum (electrospray) m/z=392 (M+1); $^1$H NMR (CDCl$_3$): 8.51 (d, 1H), 8.42 (br, 1H), 7.92 (t, 1H), 7.82 (dd, 1H), 6.84 (m, 2H), 3.63 (m, 1H), 3.02 (m, 2H), 2.44 (m, 2H), 2.04 (m, 2H), 1.87 (m, 4H), 1.60 (m, 5H), 1.11 (t, J=6.8 Hz, 3H).

Dissolve the free base (8.4 mg) in dichloromethane-methanol and add 0.02 mL of 1N HCl in ether, evaporate and dry in vacuum to give the hydrochloride salt.

19. 2,4,6-Trifluoro-N-[6-(1-propylpiperidin-4-ylcarbonyl)-pyridin-2-yl]-benzamide

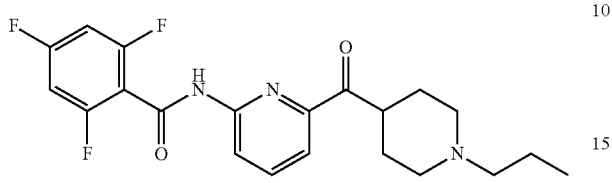

Mix 2,4,6-trifluoro-N-[6-(piperidin-4-ylcarbonyl)-pyridin-2-yl]-benzamide (50 mg), propionaldehyde (80 mg), sodium triacetoxyborohydride (38 mg) and acetic acid (21 mg) with dichloromethane (5 mL) and stir for 1.5 hrs. Dilute with methanol and load on a SCX column (10 g), wash with methanol, elute the product with 2M $NH_3$-methanol. Purify the product on a silica gel column (10 g, dichloromethane/2M $NH_3$ in methanol, gradient) to obtain the title compound as a free base (26 mg). Mass spectrum (electrospray) m/z=406 (M+1); $^1$H NMR ($CDCl_3$): 8.52 (d, 1H), 8.38 (br, 1H), 7.92 (t, 1H), 7.82 (dd, 1H), 6.82 (m, 2H), 3.61 (br, 1H), 3.00 (m, 2H), 2.34 (m, 2H), 2.11 (m, 2H), 1.87 (m, 3H), 1.60 (m, 5H), 0.90 (t, J=7.3 Hz, 3H).

Dissolve the free base (26 mg) in dichloromethane-methanol and add 0.064 mL of 1N HCl in ether, evaporate and dry under vacuum to obtain the hydrochloride salt.

20. 2,4,6-Trifluoro-N-[6-(1-cyclopropylmethyl-piperidin-4-ylcarbonyl)-pyridin-2-yl]-benzamide dihydrochloride salt

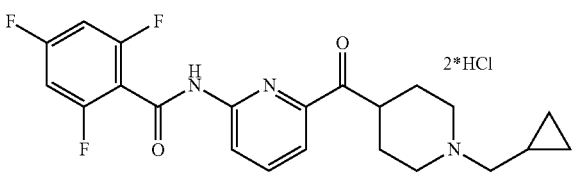 [SMILES: O=C(Nc1cccc(C(=O)C2CCN(CC3CC3)CC2)n1)c1c(F)cc(F)cc1F]

Combine 2,4,6-trifluoro-N-[6-(piperidin-4-ylcarbonyl)pyridin-2-yl]benzamide (0.05 g, 0.138 mmol), cyclopropylmethanal (0.10 g, 1.38 mmol) and dichloromethane (5 mL), and stir at ambient temperature. After 15 minutes, add glacial acetic acid (0.02 mL, 0.35 mmol) followed by sodium-triacetoxyborohydride (0.038 g, 0.18 mmol) with stirring. After 3 hrs., dilute the reaction mixture with methanol (5 mL) and load on an SCX column (10 g). Wash the column with methanol, elute with 2M ammonia/methanol, and concentrate the eluent. Purify the residue by flash chromatography, eluting with 10% ammonia/methanol in dichloromethane, to obtain the free base of the title compound (0.045 g, 77%). Dissolve the free base in dichloromethane (5 mL), treat with 1M hydrogen chloride in diethylether (0.25 mL), and concentrate the mixture to obtain the dihydrochloride salt. M.p.=140° C.; HRMS: Obs. m/z 418.1743; Calc. m/z 418.1742; $^1$H NMR ($CDCl_3$): 11.51 (bs, 1H), 10.34 (bs, 1H), 8.38 (m, 1H), 8.11 (m, 1H), 7.78 (d, 1H), 7.42 (m, 2H), 3.79 (m, 1H), 3.64 (m, 2H), 2.98 (m, 4H), 2.17 (m, 2H), 1.99 (m, 2H), 1.13 (m, 1H), 0.65 (m, 2H), 0.39 (m, 2H).

Preparations

3. N-Methylisonipecotic acid

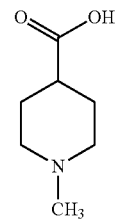

Load isonipicotic acid (1 kg, 7.74 mol), water (10 L), formaldehyde (37% solution in water, 720 g, 8.87 mol, 1.15 eq.) and wet Pd/C catalyst (10%; 55% paste, 100 g) into a stainless steel hydrogenation reactor. Pressurize the reactor with $H_2$ (3 bar) and stir the reaction mixture overnight at 200-300 rpm at 16-25° C. Stop the reaction and filter off the catalyst. Wash the filtrate with water (500 ml) and concentrate under vacuum. Distill off the remaining water from the residue using ethanol (2×1 L). Dry the solid overnight under vacuum at 50° C. to obtain the title product as an off-white solid (1087 g, 98.1% yield).

4. N-Methylisonipecotyl chloride hydrochloride

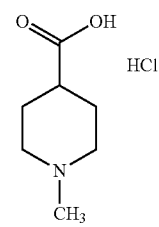

Suspend N-methylisonipicotic acid (365 g, 2.55 mol) in $CH_2Cl_2$ (3500 ml) and add a catalytic quantity of DMF (2 ml). Add oxalyl chloride (435 g, 3.42 mol, 1.35 eq.) to the reaction mixture maintaining the temperature at 20° C. Heat the suspension under reflux for 2 hrs. Cool the reaction mixture and concentrate on a rotary evaporator. Resuspend the residue in toluene (1000 ml), evaporate and dry under vacuum to yield the title product (489 g, 96%) as an off-white solid residue, which is used without further purification in the next reaction step.

5. N,N'-Dimethyl-N-methylisonipecotamide

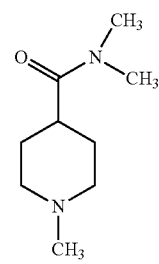

Resuspend N-methylisonipecotyl chloride hydrochloride (489 g, 2.54 mol) in anhydrous THF (5000 mL) and cool the suspension to 0-5° C. Add a solution of dimethylamine in THF (2M, 2500 ml, 2 eq.) and triethylamine (775 g, 3 eq.) dropwise to the reaction mixture maintaining the temperature below 7° C. Stir the suspension for 3 hrs. at this temperature and then allow the reaction mixture to warm to 20° C. overnight. Then cool the reaction mixture to 5° C. and 30% NaOH (600 mL) and add $CH_2Cl_2$ (2 L). Separate the organic layer from the sticky solid that is formed and redissolve the solid in water (2 L). Extract the solution with $CH_2Cl_2$ (2 L). Combine the organic fractions, concentrate to about 3500 mL, and wash twice with water (500 mL). Dry the organic layer with $Na_2SO_4$, filter, and concentrate to dryness. Dry the red oil under vacuum at room temperature to produce the title product (378.7 g, 90% yield). Treat with ether and evaporate to dryness to obtain the product as a solid.

6. 2-Bromo-6-(1-methylpiperid-4-ylcarbonyl)-pyridine

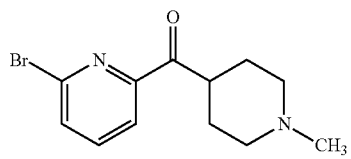

Cool methyl-tert-butyl ether (MTBE) (50 mL) ($T_{mass}$=-75° C.) under a nitrogen atmosphere, and add n-butyl litium (2.5M in n-hexane, 35 mL, 0.875 mol) to give a white suspension. Add 2,6-Dibromopyridine (20.9 g, 0.088 mol) in MTBE (210 mL) dropwise to the suspension at a rate that maintains the $T_{mass}$ under −65° C. (40 min). Stir the resulting yellow heterogeneous solution at −70° C. for 20 min. to produce a green homogeneous solution. Then add N',N-dimethyl-N-methylisonipecotamide (10 g, 0.0587 mol) in MTBE (100 mL) dropwise at a rate that maintains the $T_{mass}$ under −65° C. (20 min). After the addition is completed, agitate the mixture at −75° C. for 1 hour. Quench the reaction mixture with saturated ammonium chloride (30 mL) at 0-10° C. Neutralize the reaction mixture (pH=7) with 37% HCl (15 mL) and add additional water (50 mL). Decant the aqueous phase and extract with $CH_2Cl_2$ (3×500 mL). Combine the organic layers and wash with acidic water (pH=2) (3×500 mL). Then basify the aqueous phase with 30% NaOH (pH=12) and extract the mixture with ethyl acetate (2×500 mL). Combine the organic layers, dry with $MgSO_4$, concentrate under reduced pressure, and then vacuum dry at room temperature to provide the title product as an oil (16 g, 96% yield). Mass spectrum (electrospray) m/z=283-285 (M+1); $^1$H NMR: (400 MHz, CHLOROFORM-D) ppm 1.76 (m, 2 H) 1.91 (m, 2 H) 2.14 (m, 2 H) 2.30 (s, 3 H) 2.90 (d, J=11.85 Hz, 2 H) 3.71 (m, 1 H) 7.62 (d, J=7.54 Hz, 1 H) 7.67 (t, J=7.54 Hz, 1H) 7.95 (d, J=7.54 Hz, 1H); $^{13}$C-NMR: (100.61 MHz, Chloroform-D) ppm 28.08; 41.68; 46.36; 55.08; 121.26; 131.61; 139.25; 141.24; 153.59; 202.23.

7. 2-Amino-(6-(1-methylpiperidin-4-ylcarbonyl)-pyridine

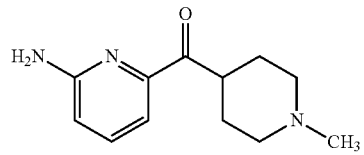

Load 2-bromo-6-(1-methylpiperidin-4-ylcarbonyl)-piperidine (20 g, 70.67 mmol, 1 eq) in 73.6 ml of 7M $NH_3$/ethylene glycol (530 mmol, 7.5 eq) into a 130 ml pressure autoclave, and add $Cu_2O$ (101 mg, 0.706 mmol, 0.01 eq) as a catalyst. Seal the autoclave and heat the reaction mixture to 85° C. at about 50 psi (345 kPa) for 20 hrs. Cool the reaction mixture to room temperature, transfer the organic layer to a 250 ml flask, and place the flask under reduce pressure to remove ammonia. Add water (70 mL) and of 30% NaOH (38 mL) and then extract the mixture with methyl t-butyl ether (MTBE)(5×100 ml). Combine the organic fractions and then dry with MgSO4, filter, and concentrate under reduce pressure to obtain crude 2-amino-(6-(1-methylpiperidin-4-ylcarbonyl)-pyridine (18.5 g).

Resuspend the crude 2-amino-(6-(1-methylpiperidin-4-ylcarbonyl)-pyridine (14.5 g, 66.2 mmol) in ethanol (30 mL), add 2.5M HCl/ethanol (100 mL), stir the mixture for 30 minutes, and then remove the solvent under reduce pressure. Resuspend the resulting solid in 125 ml isopropanol and heat under reflux for 30 minutes. Cool the reaction mixture to room temperature, filtered-off the precipitate, rinse with 20 ml isopropanol, and dry under vacuum at 50° C. to obtain 2-amino-(6-(1-methylpiperidin-4-ylcarbonyl)-pyridine 2HCl (11 g, 63% yield corrected by HPLC % w/w).

Resuspend the 2-amino-(6-(1-methylpiperidin-4-ylcarbonyl)-pyridine 2HCl (129.5 g) in ethyl acetate (100 mL) and add 10M NaOH (50 mL) and water (50 mL) to neutralize the suspension. Separate the organic layer and extract the aqueous phase with ethyl acetate (2×150 mL). Combine the organic layers, dry with $MgSO_4$, filter, and concentrate under reduce pressure to obtain the title product (21 g).

Examples

21. 2,4,6-Trifluoro-N-[6-(1-methyl-piperidin-4-yl-carbonyl)-pyridin-2-yl]-benzamide

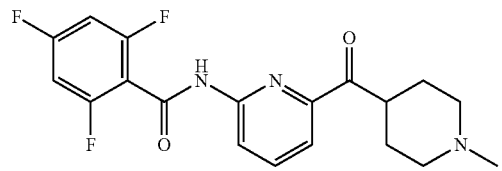 [SMILES: CN1CCC(C(=O)c2cccc(NC(=O)c3c(F)cc(F)cc3F)n2)CC1]

Add triethylamine (10.67 mL, 76.70 mmol, 2.4 eq) to a solution of 2-amino-(6-(1-methylpiperidin-4-ylcarbonyl)-pyridine (7 g, 31.96 mmol, 1 eq) in anhydrous THF (100 mL) under a nitrogen atmosphere. Add 2,4,6-triflubenzoylchloride (7.46 g, 5 mL, 38.35 mmol, 1.20 eq) dropwise at room temperature. After 2 hrs., add additional 2,4,6-triflubenzoyl-chloride (0.75 mL, 0.15 eq) and triethylamine (1.32 mL, 0.3 eq) to the reaction mixture and agitate the mixture for an additional 3 hrs. Quench the reaction with distilled water (10 mL) and 30% NaOH (15 mL). Stir the resulting biphasic system for 1 hour and then separate the phases. Extract the organic fraction by adding $H_2O$ (75 mL) and acetic acid (12 mL), followed by cyclohexane (70 mL). Wash the organic fraction with $H_2O$ (50 mL) containing acetic acid (1 mL). Combine all the aqueous fractions and washes and neutralize the mixture with 30% NaOH (15 mL). Extract with methyl-tert-butyl ether (MTBE) (3×50 mL). Combine the organic fractions and dry with $MgSO_4$, filter, concentrate under reduce pressure, and vacuum dry at room temperature, to obtain the title compound as a light-brown solid (11.031 g, 91% yield). Mass spectrum (Electrospray) m/z=378 (M+1); $^1H$ NMR (250 MHz, Chloroform-D) ppm 1.54 (m, 2 H) 2.02 (m, 2 H) 2.13 (t, J=11.48 Hz, 2 H) 2.29 (s, 3 H) 2.80 (m, J=11.96 Hz, 1 H) 3.56 (m, 1 H) 4.26 (d, J=7.87 Hz, 1 H) 6.17 (d, J=8.50 Hz, 1 H) 6.75 (m, 2 H) 7.45 (t, J=7.87 Hz, 1 H) 7.53 (m, 1 H) 7.95 (s, 1 H); $^{13}C$-NMR: (62.90 MHz, Chloroform-D) ppm 202.78; 162.0 (m C—F-couplings); 162.6 (dm C—F-couplings); 160.1 (m C—F-couplings); 158.1; 150.0; 139.7; 119.3; 117.9; 110.2 (m C—F-couplings); 100.9 (m C—F-couplings); 55.2; 46.5; 41.9; 28.1

22. 2,4,6-Trifluoro-N-[6-(1-methyl-piperidin-4-yl-carbonyl)-pyridin-2-yl]-benzamide mono-hydrochloride salt

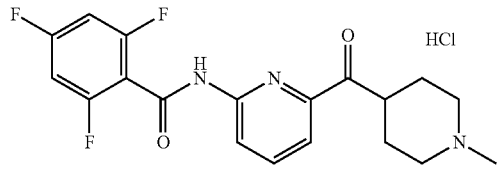 [SMILES: CN1CCC(C(=O)c2cccc(NC(=O)c3c(F)cc(F)cc3F)n2)CC1 ; Cl]

Dissolve 2,4,6-trifluoro-N-[6-(1-methylpiperidin-4-ylcarbonyl)-pyridin-2-yl]-benzamide—free base (5 g, 23.26 mmol) in isopropanol (50 mL) at room temperature and add a solution of 3.3 M diethylether/HCl (8 mL). Heat the reaction mixture under reflux for 30 minutes. Cool the reaction mixture to room temperature and agitate for 2 hrs. Filter the resulting white precipitate and rinse with isopropanol (5 mL). Dry the residual solid under reduce pressure at 40° C. overnight to obtain the title compound (5.12 g, 93% yield). M.p. 223-224° C. (sublimation); $^1H$ NMR (400 MHz, d6-DMSO) d ppm 1.94 (m, 2 H) 2.14 (m, J=11.15 Hz, 2 H) 2.74 (s, 3 H) 2.99 (m, J=9.19 Hz, 2 H) 3.49 (m, J=11.15 Hz, 2 H) 3.77 (m, 1 H) 7.41 (t, J=8.71 Hz, 2 H) 7.78 (d, J=7.43 Hz, 1 H) 8.10 (t, J=7.92 Hz, 1 H) 8.37 (d, J=6.85 Hz, 1 H) 10.50 (s, 1 H) 11.51 (s, 1 H); $^{13}C$-NMR: (100.61 MHz, Chloroform-D) ppm 200.7; 130.6-158.0 (m, C—F-couplings); 150.4; 150.1; 140.2; 118.5; 118.2; 111.9; 101.3 (t, C—F couplings); 52.8; 42.6; 25.2

23. 2,4,6-Trifluoro-N-[6-(1-methyl-piperidine-4-carbonyl)-pyridin-2-yl]-benzamide hemi-succinate salt

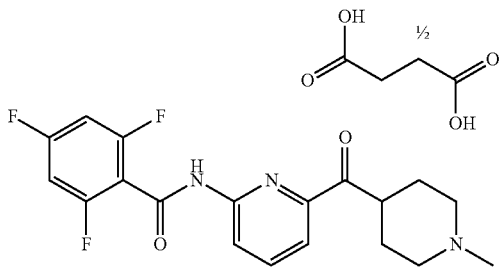 [SMILES: CN1CCC(C(=O)c2cccc(NC(=O)c3c(F)cc(F)cc3F)n2)CC1 ; O=C(O)CCC(=O)O]

Add succinic acid (0.25 g, 2.148 mmol, 0.5 eq) to a solution of 2,4,6-trifluoro-N-[6-(1-methyl-piperidin-4-ylcarbonyl)-pyridin-2-yl]-benzamide—free base (1.62 g, 4.297 mmol, 1 eq) in acetone (16.2 mL), at room temperature. Warm the solution under reflux for 30 minutes. Cool the solution to room temperature and filter off the resulting white precipitate. Rinse the precipitate with acetone (0.2 mL) and dry under vacuum at 50° C. for 16 hours to provide the title compound (1.5 g, 80% yield). M.p. 198.5° C.; mass spectrum (Electrospray) m/z=495.45

The following examples are prepared by combinatorial chemistry techniques as follows:

Examples 24-54

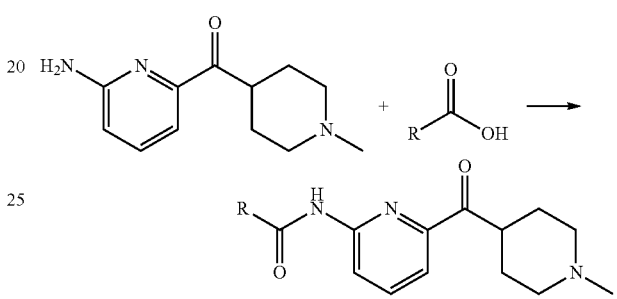

Combine R-acid (300 μL of 0.5M solution in dimethylformamide (DMF)), HATU (57 mg, 0.15 mmol), collidine (19 μL, 0.15 mmol), 2-amino-(6-(1-methylpiperidin-4-ylcarbonyl)-pyridine and DMF (1.5 mL), and agitate for 48 hr. Dilute the reaction mixture with 10% acetic acid in methanol (0.5 mL). Load the resulting reaction mixture onto a 2 g SCX column. Wash the column thoroughly with methanol and then elute with 1 M ammonia in methanol. Concentrate the eluent and further purify the product by high-throughput mass guided chromatography. This procedure is repeated in parallel for examples 24-54.

Examples 55-58

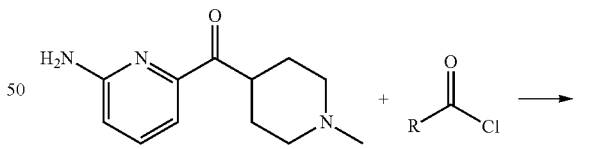

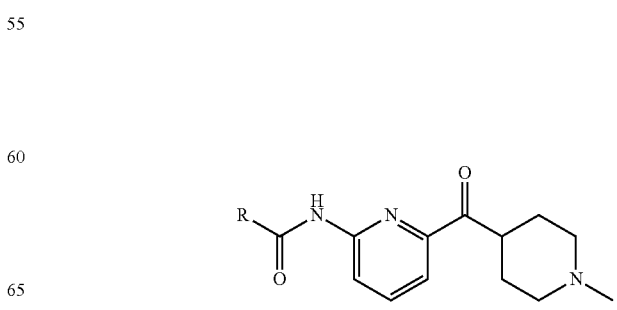

Heat R-acid chloride (300 μL of 0.5M solution in pyridine) to 55° C., add 2-amino-(6-(1-methylpiperidin-4-ylcarbonyl)-pyridine (200 μL of 0.5M solution in pyridine), and continue heating the reaction mixture for 24 hr. Concentrate the reaction mixture and then dilute with 10% Acetic acid in methanol (0.5 mL) and methanol (0.5 mL). Load the resulting reaction mixture directly onto a 2 g SCX column. Thoroughly wash the column with methanol and then elute the column with 1 M ammonia in methanol. Concentrate the eluent and then further purify the product by high-throughput mass guided chromatography. This procedure is repeated in parallel for examples 55-58.

Examples 59-71

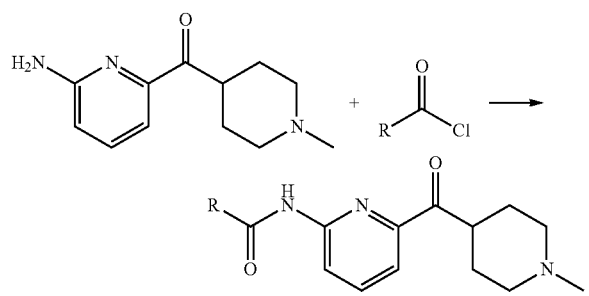

Heat 2-amino-(6-(1-methylpiperidin-4-ylcarbonyl)-pyridine (200 μL of 0.5M solution in pyridine) to 55° C. then add R-acid chloride (0.10 mmol), heat for 2 hr. Concentrate the reaction mixture and then dilute with 10% Acetic acid in methanol (0.5 mL) and methanol (0.5 mL). Load the resulting reaction mixture directly onto a 2 g SCX column. Thoroughly wash the column with methanol and then elute the column with 1 M ammonia in methanol. Concentrate the eluent and then further purify the product by high-throughput mass guided chromatography. This procedure is repeated in parallel for examples 59-71.

Recombinant chemistry compounds are characterized by liquid chromatography/mass spectroscopy on a Shimadzu QP8000™. Examples 24-45 and 55-58 are run with a Metachem™ C18 column (monochrom 3 micron, 2.5×25 cm) using a 10-90% solvent B gradient in 4.5 min., where solvent A is 0.1% trifluoroacetic acid in water and solvent B is 0.1% trifluoroacetic acid in acetonitrile. Examples 46-54 and 59-71 are run with a Metachem™ C18 column (monochrom 5 micron, 4.6×50 cm) using a 10-80% solvent B gradient in 9 min., where solvent A is 0.1% trifluoroacetic acid in water and solvent B is 0.08% trifluoroacetic acid in acetonitrile.

| 24 | N-[6-(1-Methyl-piperidin-4-ylcarbonyl)-pyridin-2-yl]-thiophene-2-amide | 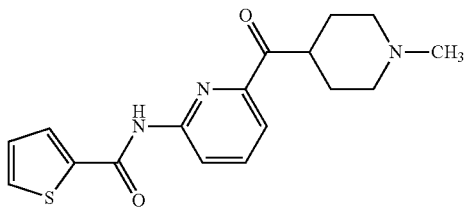 | LCMS Rf 2.871 min at 254 nm, 2.871 min at 190 nm, m/e 330 (M + 1). |
|---|---|---|---|
| 25 | N-[6-(1-Methyl-piperidin-4-ylcarbonyl)-pyridin-2-yl]-furan-2-amide | 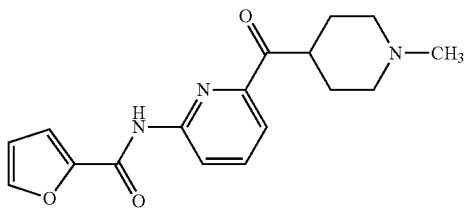 [SMILES: CN1CCC(C(=O)c2cccc(NC(=O)c3ccco3)n2)CC1] | LCMS Rf 2.454 min at 254 nm, 2.454 min at 190 nm, m/e 314 (M + 1). |
| 26 | 2-Chloro-N-[6-(1-methyl-piperidin-4-ylcarbonyl)-pyridin-2-yl]-benzamide | 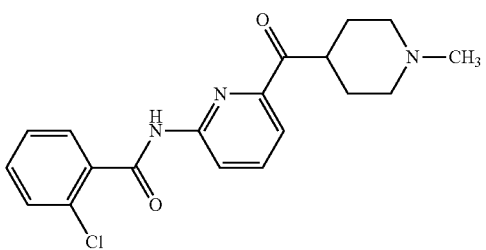 [SMILES: CN1CCC(C(=O)c2cccc(NC(=O)c3ccccc3Cl)n2)CC1] | LCMS Rf 3.080 min at 254 nm, 3.080 min at 190 nm, m/e 358 (M + 1). |

-continued

| | | | |
|---|---|---|---|
| 27 | N-[6-(1-Methyl-piperidin-4-ylcarbonyl)-pyridin-2-yl]-furan-3-amide | 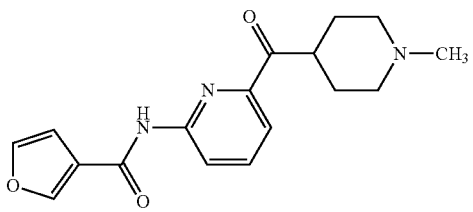 [SMILES: CN1CCC(C(=O)c2cccc(NC(=O)c3ccoc3)n2)CC1] | LCMS Rf 2.448 min at 254 nm, 2.448 min at 190 nm, m/e 314 (M + 1). |
| 28 | 3,4-Difluoro-N-[6-(1-methyl-piperidin-4-ylcarbonyl)-pyridin-2-yl]-benzamide | 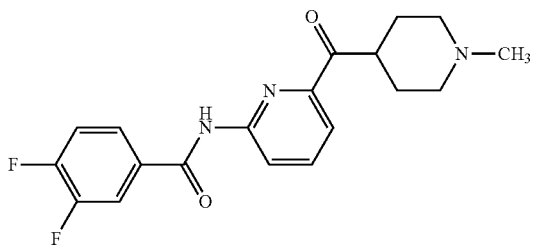 [SMILES: CN1CCC(C(=O)c2cccc(NC(=O)c3ccc(F)c(F)c3)n2)CC1] | LCMS Rf 4.47 min at 254 nm, m/e 360 (M + 1). |
| 29 | N-[6-(1-Methyl-piperidin-4-ylcarbonyl)-pyridin-2-yl]-isonicotinamide | 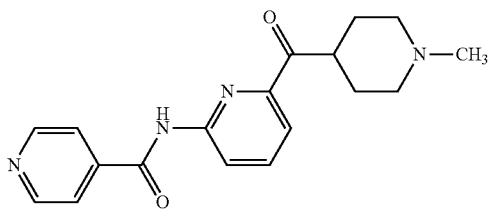 [SMILES: CN1CCC(C(=O)c2cccc(NC(=O)c3ccncc3)n2)CC1] | LCMS Rf 2.890 min at 254 nm, 2.890 min at 190 nm, m/e 325 (M + 1). |
| 30 | 2-Methyl-N-[6-(1-methyl-piperidin-4-ylcarbonyl)-pyridin-2-yl]-benzamide | 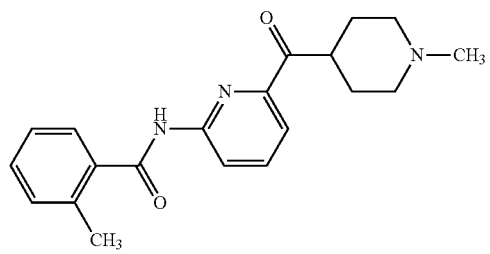 [SMILES: Cc1ccccc1C(=O)Nc1cccc(C(=O)C2CCN(C)CC2)n1] | LCMS Rf 3.092 min at 254 nm, 3.092 min at 190 nm, m/e 338 (M + 1). |
| 31 | 2-Bromo-N-[6-(1-methyl-piperidin-4-ylcarbonyl)-pyridin-2-yl]-benzamide | 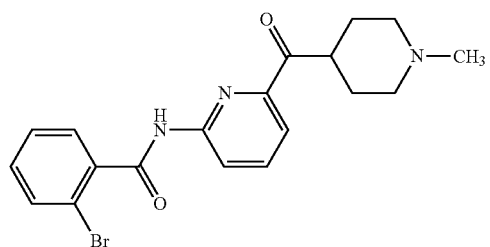 [SMILES: CN1CCC(C(=O)c2cccc(NC(=O)c3ccccc3Br)n2)CC1] | LCMS Rf 3.132 min at 254 nm, 3.132 min at 190 nm, m/e 402 (M + 1). |
| 32 | 2-trifluoromethoxy-N-[6-(1-methyl-piperidin-4-ylcarbonyl)-pyridin-2-yl]-benzamide | 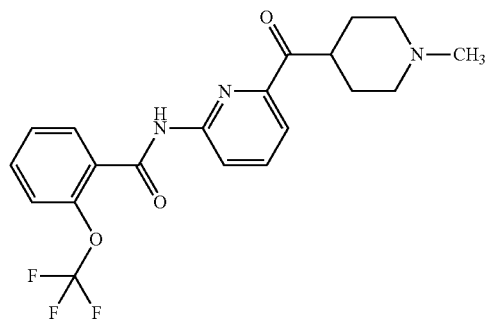 | LCMS Rf 2.771 min at 254 nm, 2.771 min at 190 nm, m/e 330 (M + 1). |

-continued

| | | | |
|---|---|---|---|
| 33 | 2-Fluoro-N-[6-(1-methyl-piperidin-4-ylcarbonyl)-pyridin-2-yl]-isonicotinamide | 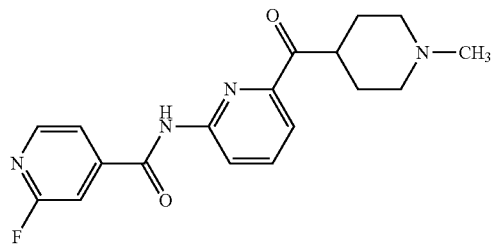 [SMILES: CN1CCC(C(=O)c2cccc(NC(=O)c3ccnc(F)c3)n2)CC1] | LCMS Rf 2.669 min at 254 nm, 2.669 min at 190 nm, m/e 343 (M + 1). |
| 34 | 4-Chloro-2-methoxy-N-[6-(1-methyl-piperidin-4-ylcarbonyl)-pyridin-2-yl]-benzamide | 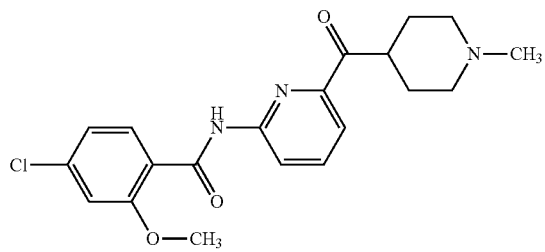 | LCMS Rf 3.665 min at 254 nm, 3.664 min at 190 nm, m/e 387 (M + 1). |
| 35 | 2-Ethoxy-N-[6-(1-methyl-piperidin-4-ylcarbonyl)-pyridin-2-yl]-benzamide | 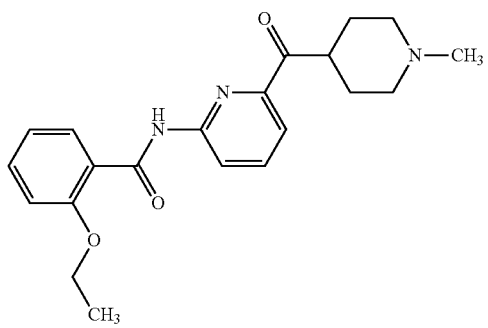 [SMILES: CCOc1ccccc1C(=O)Nc1cccc(C(=O)C2CCN(C)CC2)n1] | LCMS Rf 3.519 min at 254 nm, 3.520 min at 190 nm, m/e 367 (M + 1). |
| 36 | 2-Phenoxy-N-[6-(1-methyl-piperidin-4-ylcarbonyl)-pyridin-2-yl]-benzamide | 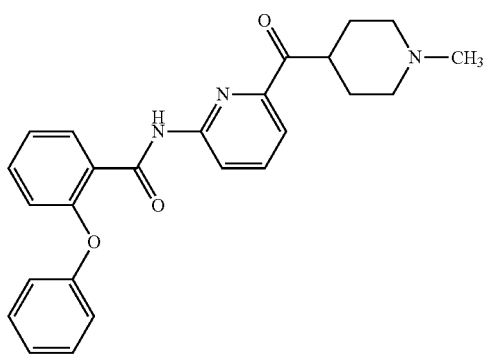 [SMILES: CN1CCC(C(=O)c2cccc(NC(=O)c3ccccc3Oc3ccccc3)n2)CC1] | LCMS Rf 3.841 min at 254 nm, 3.838 min at 190 nm, m/e 415 (M + 1). |
| 37 | 2-Methoxy-5-chloro-N-[6-(1-methyl-piperidin-4-ylcarbonyl)-pyridin-2-yl]-benzamide | 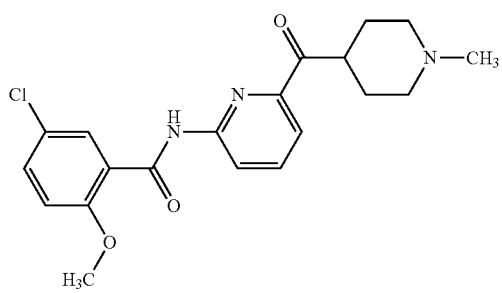 [SMILES: COc1ccc(Cl)cc1C(=O)Nc1cccc(C(=O)C2CCN(C)CC2)n1] | LCMS Rf 3.661 min at 254 nm, 3.666 min at 190 nm, m/e 387 (M + 1). |

-continued

| | | | |
|---|---|---|---|
| 38 | 2-Methoxy-4-methylsulfanyl-N-[6-(1-methylpiperidin-4-ylcarbonyl)-pyridin-2-yl]-benzamide | 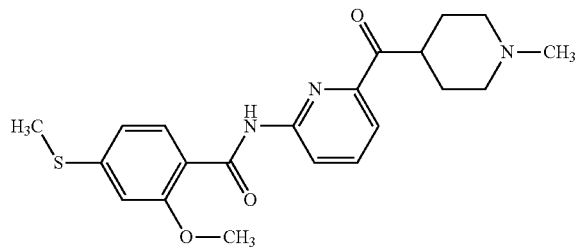 | LCMS Rf 3.683 min at 254 nm, 3.692 min at 190 nm, m/e 399 (M + 1). |
| 39 | N-[6-(1-Methyl-piperidin-4-ylcarbonyl)-pyridin-2-yl]-2,3-Dihydrobenzofuran-7-amide | 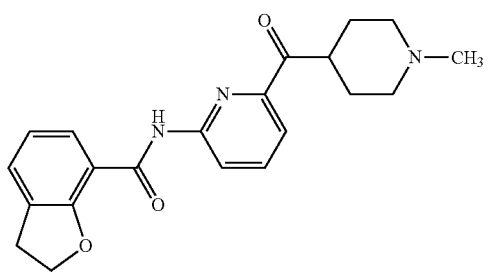 [SMILES: CN1CCC(C(=O)c2cccc(NC(=O)c3cccc4c3OCC4)n2)CC1] | LCMS Rf 3.381 min at 254 nm, 3.381 min at 190 nm, m/e 365 (M + 1). |
| 40 | 2-Benzyloxy-N-[6-(1-methyl-piperidin-4-ylcarbonyl)-pyridin-2-yl]-benzamide | 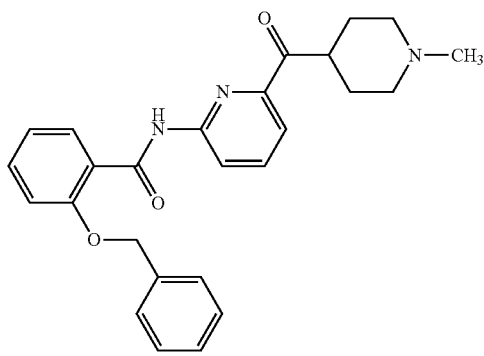 [SMILES: CN1CCC(C(=O)c2cccc(NC(=O)c3ccccc3OCc3ccccc3)n2)CC1] | LCMS Rf 4.086 min at 254 nm, 4.089 min at 190 nm, m/e 429 (M + 1). |
| 41 | 2-Propoxy-N-[6-(1-methyl-piperidin-4-ylcarbonyl)-pyridin-2-yl]-benzamide | 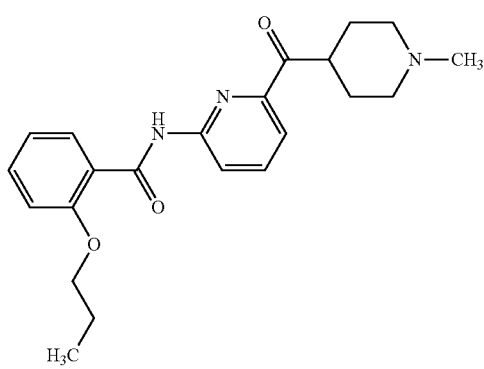 [SMILES: CCCOc1ccccc1C(=O)Nc1cccc(C(=O)C2CCN(C)CC2)n1] | LCMS Rf 3.811 min at 254 nm, 3.813 min at 190 nm, m/e 381 (M + 1). |
| 42 | 2,2-Difluoro-N-[6-(1-methyl-piperidin-4-ylcarbonyl)-pyridin-2-yl]-benzo[1,3]dioxole-4-amide | 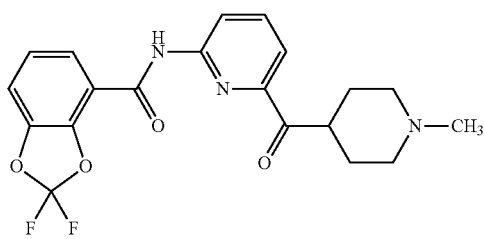 [SMILES: CN1CCC(C(=O)c2cccc(NC(=O)c3cccc4c3OC(F)(F)O4)n2)CC1] | LCMS Rf 3.531 min at 254 nm, 3.534 min at 190 nm, m/e 403 (M + 1). |

| | | | |
|---|---|---|---|
| 43 | 2-(2-Methoxy-ethoxy)-4-methoxy-N-[6-(1-methyl-piperidin-4-ylcarbonyl)-pyridin-2-yl]-benzamide | 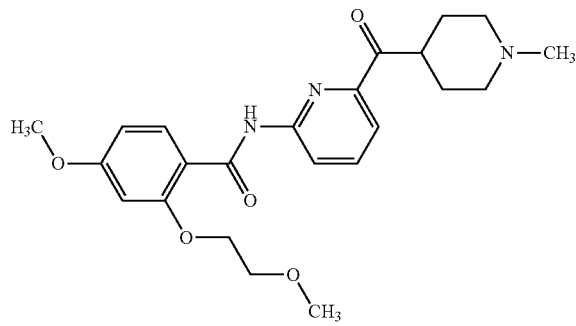 | LCMS Rf 3.552 min at 254 nm, 3.556 min at 190 nm, m/e 427 (M + 1). |
| 44 | 2-Methoxy-5-bromo-N-[6-(1-methyl-piperidin-4-ylcarbonyl)-pyridin-2-yl]-benzamide | 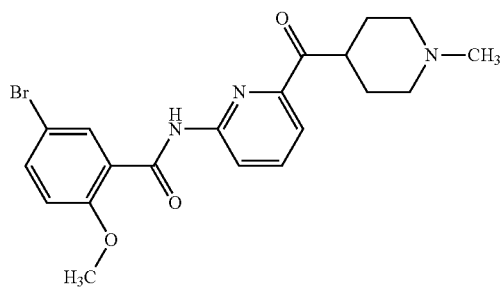 | LCMS Rf 3.742 min at 254 nm, 3.742 min at 190 nm, m/e 432 (M + 1). |
| 45 | 2-(4,6-Dimethoxy-pyrimidin-2-yloxy)-N-[6-(1-methyl-piperidin-4-ylcarbonyl)-pyridin-2-yl]-benzamide | 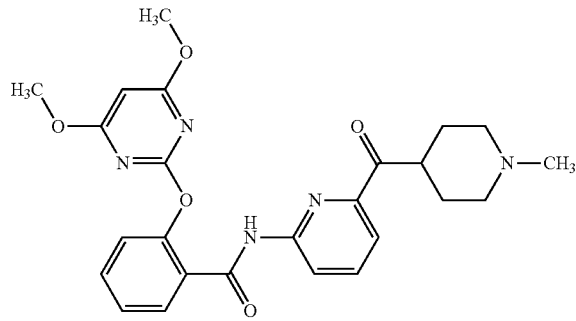 | LCMS Rf 3.428 min at 254 nm, 3.425 min at 190 nm, m/e 477 (M + 1). |
| 46 | 2-Ethoxy-N-[6-(1-methyl-piperidin-4-ylcarbonyl)-pyridin-2-yl]-nicotinamide | 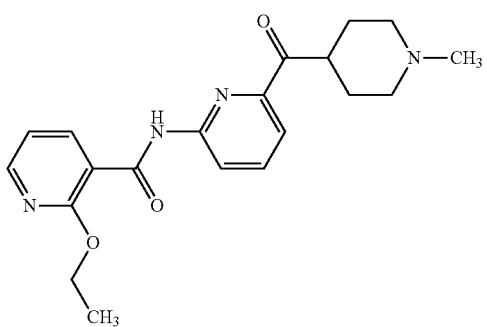 [SMILES: CCOc1ncccc1C(=O)Nc1cccc(C(=O)C2CCN(C)CC2)n1] | LCMS Rf 1.56 min at 254 nm, m/e 368 (M + 1). |
| 47 | 2-Phenoxy-N-[6-(1-methyl-piperidin-4-ylcarbonyl)-pyridin-2-yl]-nicotinamide | 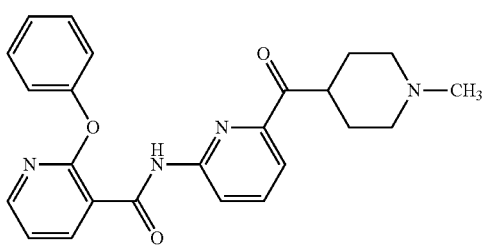 [SMILES: CN1CCC(C(=O)c2cccc(NC(=O)c3cccnc3Oc3ccccc3)n2)CC1] | LCMS Rf 1.61 min at 254 nm, m/e 416 (M + 1). |

| | | | | |
|---|---|---|---|---|
| 48 | 3-Acetyl-N-[6-(1-methyl-piperidin-4-ylcarbonyl)-pyridin-2-yl]-thiazolidine-4-amide | 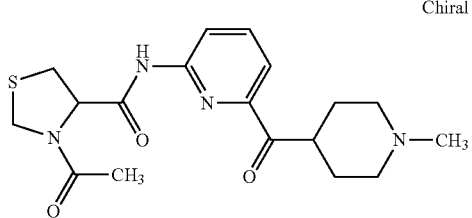 [SMILES: CC(=O)N1CSCC1C(=O)Nc1cccc(C(=O)C2CCN(C)CC2)n1] | Chiral | LCMS Rf 1.23 min at 254 nm, m/e 376 (M + 1). |
| 49 | 2-Phenylsulfanyl-N-[6-(1-methyl-piperidin-4-ylcarbonyl)-pyridin-2-yl]-nicotinamide | 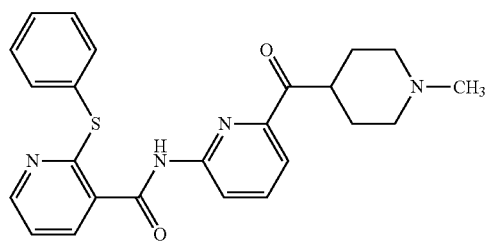 | | LCMS Rf 1.59 min at 254 nm, m/e 432 (M + 1). |
| 50 | 2-(2,2,2-Trifluoroethoxy)-5-methoxy-N-[6-(1-methyl-piperidin-4-ylcarbonyl)-pyridin-2-yl]-benzamide | 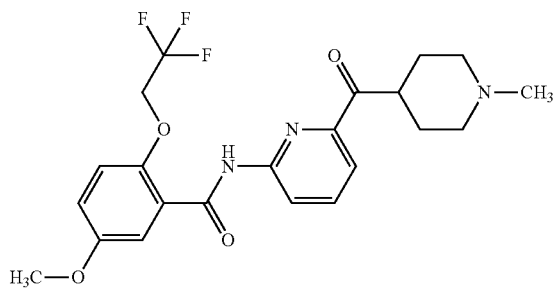 | | LCMS Rf 1.69 min at 254 nm, m/e 451 (M + 1). |
| 51 | 2-Methoxy-6-methyl-N-[6-(1-methyl-piperidin-4-ylcarbonyl)-pyridin-2-yl]-benzamide | 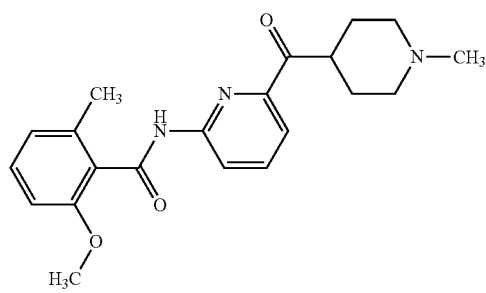 [SMILES: COc1cccc(C)c1C(=O)Nc1cccc(C(=O)C2CCN(C)CC2)n1] | | LCMS Rf 1.50 min at 254 nm, m/e 367 (M + 1). |
| 52 | 4-Methoxycarbonyl-N-[6-(1-methyl-piperidin-4-ylcarbonyl)-pyridin-2-yl]-benzamide | 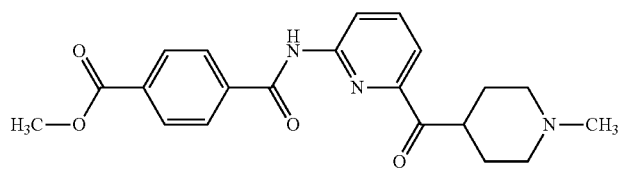 | | LCMS Rf 1.53 min at 254 nm, m/e 381 (M + 1). |
| 53 | N-[6-(1-Methyl-piperidin-4-ylcarbonyl)-pyridin-2-yl]-Cyclobutylformamide | 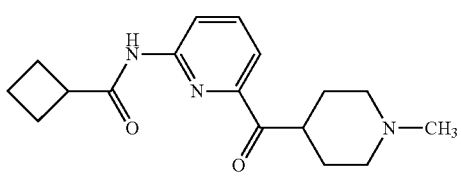 [SMILES: CN1CCC(C(=O)c2cccc(NC(=O)C3CCC3)n2)CC1] | | LCMS Rf 1.31 min at 254 nm, m/e 301 (M + 1). |

| | | | |
|---|---|---|---|
| 54 | 2-(2-Chloro-1,1,2-trifluoroethoxy)-N-[6-(1-methyl-piperidin-4-ylcarbonyl)-pyridin-2-yl]-benzamide | 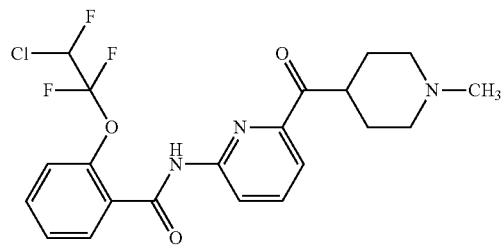 [SMILES: CN1CCC(C(=O)c2cccc(NC(=O)c3ccccc3OC(F)(F)C(F)Cl)n2)CC1] | LCMS Rf 1.64 min at 254 nm, m/e 455 (M + 1). |
| 55 | N-[6-(1-Methyl-piperidin-4-ylcarbonyl)-pyridin-2-yl]-butanamide | 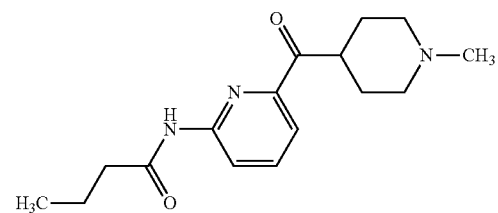 [SMILES: CCCC(=O)Nc1cccc(C(=O)C2CCN(C)CC2)n1] | LCMS Rf 2.23 min at 254 nm, m/e 290 (M + 1). |
| 56 | N-[6-(1-methyl-piperidin-4-ylcarbonyl)-pyridin-2-yl]-cyclohexylformamide | 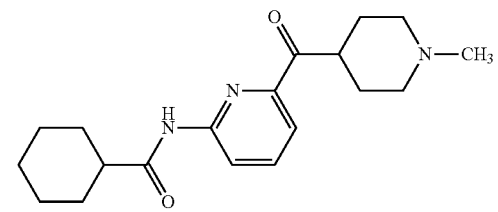 [SMILES: CN1CCC(C(=O)c2cccc(NC(=O)C3CCCCC3)n2)CC1] | LCMS Rf 4.23 min at 254 nm, m/e 330 (M + 1). |
| 57 | N-[6-(1-Methyl-piperidin-4-ylcarbonyl)-pyridin-2-yl]-3-phenyl-propanamide | 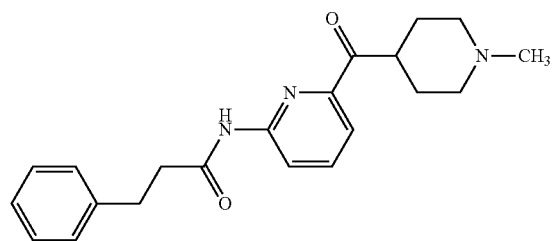 [SMILES: CN1CCC(C(=O)c2cccc(NC(=O)CCc3ccccc3)n2)CC1] | LCMS Rf 4.86 min at 254 nm, m/e 352 (M + 1). |
| 58 | 2,6-Difluoro-N-[6-(1-methyl-piperidin-4-ylcarbonyl)-pyridin-2-yl]-benzamide | 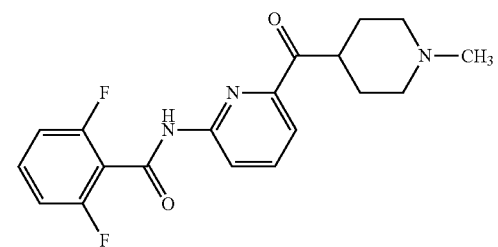 | LCMS Rf 4.05 min at 254 nm, m/e 360 (M + 1). |
| 59 | 2-Chloro-N-[6-(1-methyl-piperidin-4-ylcarbonyl)-pyridin-2-yl]-benzamide | 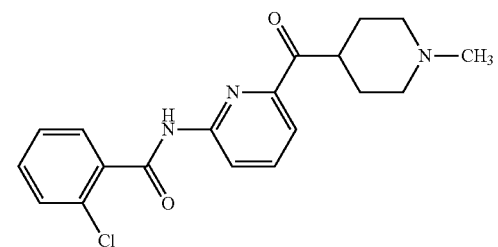 | LCMS Rf 1.47 min at 254 nm, m/e 357 (M + 1). |

| | | | |
|---|---|---|---|
| 60 | 2,5-Difluoro-N-[6-(1-methyl-piperidin-4-ylcarbonyl)-pyridin-2-yl]-benzamide | 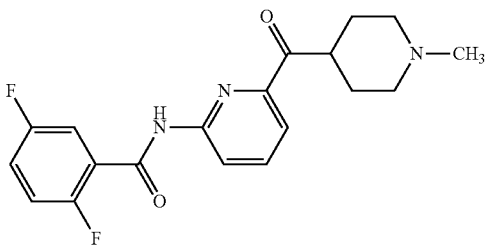 [SMILES: CN1CCC(C(=O)c2cccc(NC(=O)c3cc(F)ccc3F)n2)CC1] | LCMS Rf 1.52 min at 254 nm, m/e 359 (M + 1). |
| 61 | 3,4-Difluoro-N-[6-(1-methyl-piperidin-4-ylcarbonyl)-pyridin-2-yl]-benzamide | 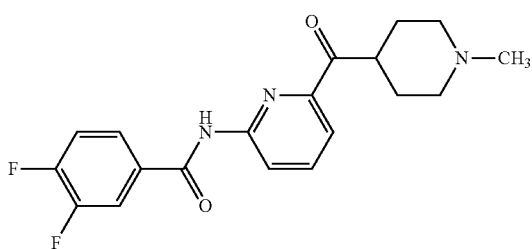 [SMILES: CN1CCC(C(=O)c2cccc(NC(=O)c3ccc(F)c(F)c3)n2)CC1] | LCMS Rf 1.54 min at 254 nm, m/e 359 (M + 1). |
| 62 | 2-Trifluoromethyl-4-fluoro-N-[6-(1-methyl-piperidin-4-ylcarbonyl)-pyridin-2-yl]-benzamide | 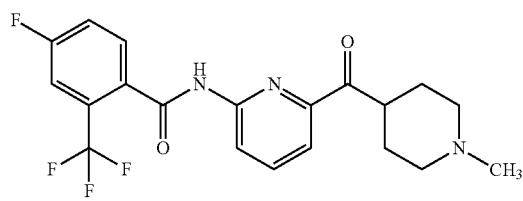 [SMILES: CN1CCC(C(=O)c2cccc(NC(=O)c3ccc(F)cc3C(F)(F)F)n2)CC1] | LCMS Rf 1.57 min at 254 nm, m/e 409 (M + 1). |
| 63 | 2-Fluoro-6-trifluoromethyl-N-[6-(1-methyl-piperidin-4-ylcarbonyl)-pyridin-2-yl]-benzamide | 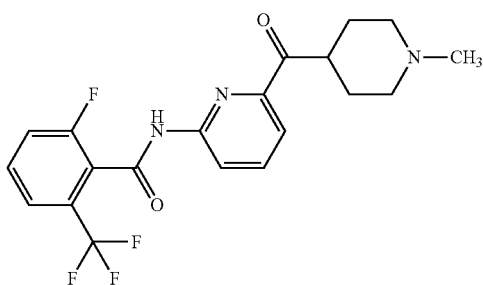 [SMILES: CN1CCC(C(=O)c2cccc(NC(=O)c3c(F)cccc3C(F)(F)F)n2)CC1] | LCMS Rf 1.60 min at 254 nm, m/e 409 (M + 1). |
| 64 | 2,3,4-Trifluoro-N-[6-(1-methyl-piperidin-4-ylcarbonyl)-pyridin-2-yl]-benzamide | 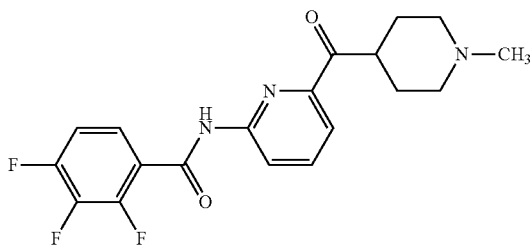 | LCMS Rf 1.57 min at 254 nm, m/e 377 (M + 1). |
| 65 | 2,4,5-Trifluoro-N-[6-(1-methyl-piperidin-4-ylcarbonyl)-pyridin-2-yl]-benzamide | 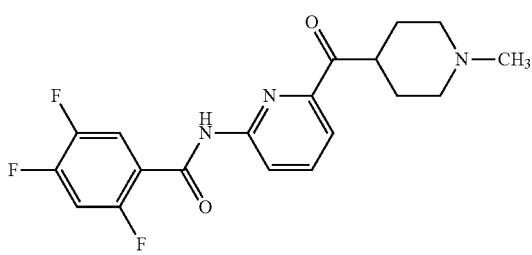 [SMILES: CN1CCC(C(=O)c2cccc(NC(=O)c3cc(F)c(F)cc3F)n2)CC1] | LCMS Rf 1.56 min at 254 nm, m/e 377 (M + 1). |

-continued

| | | | |
|---|---|---|---|
| 67 | 3-Chloro-N-[6-(1-methyl-piperidin-4-ylcarbonyl)-pyridin-2-yl]-thiophene-2-amide | 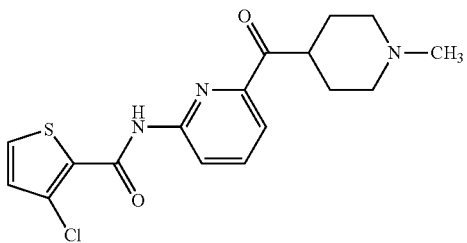 [SMILES: CN1CCC(C(=O)c2cccc(NC(=O)c3sccc3Cl)n2)CC1] | LCMS Rf 1.67 min at 254 nm, m/e 363 (M + 1). |
| 68 | 2,6-Dichloro-N-[6-(1-methyl-piperidin-4-ylcarbonyl)-pyridin-2-yl]-benzamide | 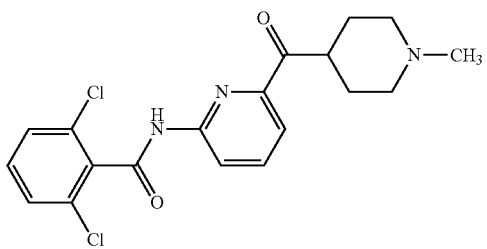 [SMILES: CN1CCC(C(=O)c2cccc(NC(=O)c3c(Cl)cccc3Cl)n2)CC1] | LCMS Rf 1.57 min at 254 nm, m/e 391 (M + 1). |
| 69 | 2-Fluoro-4-trifluoromethyl-N-[6-(1-methyl-piperidin-4-ylcarbonyl)-pyridin-2-yl]-benzamide | 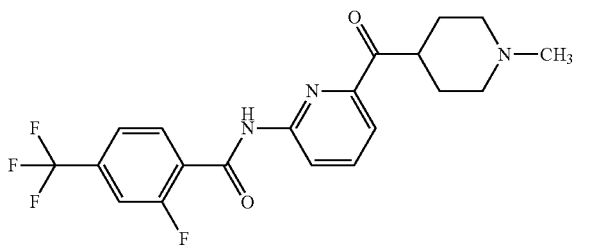 [SMILES: CN1CCC(C(=O)c2cccc(NC(=O)c3ccc(C(F)(F)F)cc3F)n2)CC1] | LCMS Rf 1.67 min at 254 nm, m/e 409 (M + 1). |
| 70 | N-[6-(1-methyl-piperidin-4-ylcarbonyl)-pyridin-2-yl]-Cyclopentylformamide | 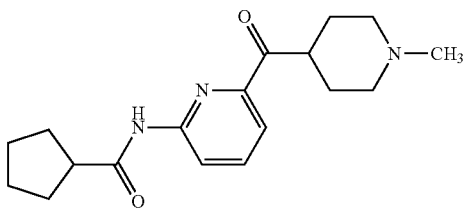 [SMILES: CN1CCC(C(=O)c2cccc(NC(=O)C3CCCC3)n2)CC1] | LCMS Rf 3.06 min at 254 nm, m/e 315 (M + 1). |
| 71 | N-[6-(1-Methyl-piperidin-4-ylcarbonyl)-pyridin-2-yl]-nicotinamide | 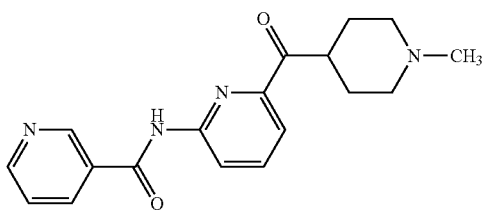 [SMILES: CN1CCC(C(=O)c2cccc(NC(=O)c3cccnc3)n2)CC1] | LCMS Rf 2.5 min at 254 nm, m/e 324 (M + 1). |

Preparations

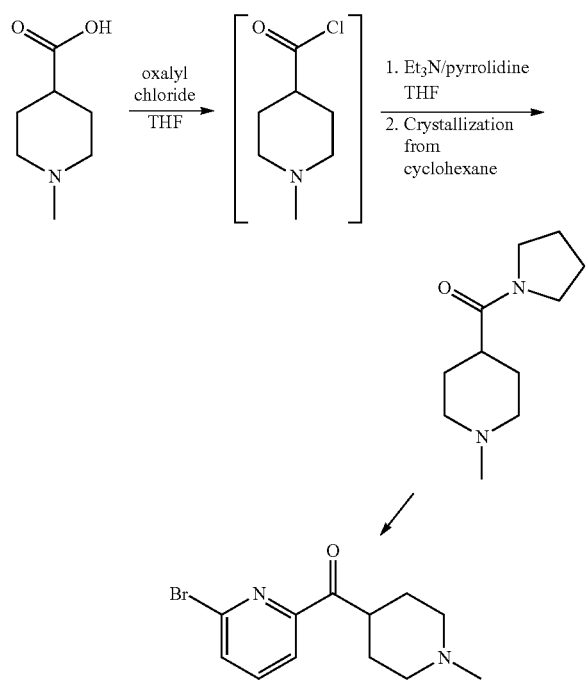

7. 1-Methyl-4-(pyrrolidin-1-yl-carbonyl)-piperidine

Add oxalyl chloride (5.08 mL, 0.058 mol) dropwise to a suspension of 1-methyl-4-carboxypiperidine HCl (10 g, 0.056 mol) in THF (100 mL) in the presence of a catalytic amount of DMF (0.1 mL) at room temperature. Stir for 1 hr. and then heat the mixture at reflux until gas emission stops (about 1 hr.). Cool the white suspension to 5° C. and add a solution of pyrrolidine (7.92 g, 0.111 mol) and triethylamine (16.9 g, 0.167 mol) dropwise over 30 min at a temperature between 5 and 13° C. Stir the suspension for 30 min. at 10° C. and then warm to room temperature. Quench the reaction mixture by adding 30% NaOH (20 mL, 0.2 mol) and water (10 mL). Decant the aqueous layer and extract with THF (200 mL). Combine the organic layers, dry over $Na_2CO_3$, and evaporate under vacuum at 40° C. Solubilize the resulting oil in cyclohexane (200 mL). Evaporate under reduced pressure at 40° C. to give a white solid (11 g). 1-Teat the white solid (11 g) under reflux in cyclohexane (50 mL) until completely dissolved. Cool the solution to room temperature and stir at room temperature for 2 hr. Filter the suspension wash the crystals with cyclohexane (10 mL). Dry the white crystals under reduced pressure at 40° C. to provide the title intermediate (7.76 g, 75% yield).

8. 2-Bromo-6-(1-methylpiperidin-4-ylcarbonyl)-pyridine

Add a solution of n-butyllithium (1.9M in n-hexane, 4 ml, 7.6 mmol) to a solution of 2,6-dibromopyridine (1.81 g, 7.64 mmol) in MTBE (20 mL) dropwise under nitrogen, over 20 min., maintaining the temperature between −72 and −67° C. Stir the yellow heterogeneous solution at −70° C. for 20 min. to provide a green homogeneous solution. Add a solution of 1-methyl-4-(pyrrolidin-1-yl-carbonyl)piperidine (1 g, 5.09 mmol) in 10 mL MTBE dropwise over 20 min., maintaining the temperature below −69° C. Stir the yellow mixture at −75° C. for 1 hr. Quench the reaction mixture with a saturated solution of ammonium chloride (5 mL) between 0 and 10° C. Acidify the mixture to pH 2 with fuming HCl (2 mL). Extract the organic layer. Wash the aqueous phase with MTBE (50 mL), make the aqueous layer basic with a solution of 30% NaOH, and extract with ethyl acetate (2×50 mL). Combine the organic layers, dry over $MgSO_4$, and concentrate under reduced pressure at 40° C. to provide the title intermediate as an oil (1.23 g, 85% yield).

The compounds of this invention are useful for increasing activation of the 5-$HT_{1F}$ receptor. An increase in the activation of the 5-$HT_{1F}$ is useful for treating a variety of disorders which have been linked to decreased neurotransmission of serotonin in mammals, e.g., migraine headaches. See U.S. Pat. No. 5,708,008 demonstrating the nexus between activation of the 5-$HT_{1F}$ receptor and migraine. To demonstrate the use of the compounds of the present invention in the treatment of migraine, their ability to bind to the 5-$HT_{1F}$ receptor subtype was determined. The ability of the compounds of this invention to bind to the 5-$HT_{1F}$ receptor subtype was measured essentially as described in N. Adham, et al., *Proceedings of the National* 15 *Academy of Sciences* (USA), 90:408-412, 1993.

Membrane Preparation:

Membranes were prepared from transfected Ltk-cells (transfected with the human 5-$HT_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH 7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The resulting pellet was washed once in ice-cold Tris wash buffer and resuspended in a final buffer containing 50 mM Tris HCl and 0.5 mM EDTA, pH 7.4 at 23° C. Membrane preparations were kept on ice and utilized within two hours for the radioligand binding assays. Protein concentrations were determined by the method of Bradford. *Anal. Biochem.,* 72:248-254, 1976.

Radioligand Binding:

[$^3$H] 5-HT binding was performed using slight modifications of the 5-$HT_{1D}$ assay conditions reported by Herrick-Davis and Titeler (*J. Neurochem.,* 50:1624-1631, 1988) with the omission of masking ligands. Radioligand binding studies were achieved at 37° C. in a total volume of 250 μL of buffer (50 mM Tris, 10 mM $MgCl_2$, 0.2 mM EDTA, 10 μM pargyline, 0.1% ascorbate, pH 7.4 at 37° C.) in 96 well microtiter plates. Saturation studies were conducted using [$^3$H] 5-HT at 12 different concentrations ranging from 0.5 nM to 100 nM. Displacement studies were performed using 4.5-5.5 nM [$^3$H] 5-HT. The binding profile of drugs in competition experiments was accomplished using 6-12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10-20 μg). The reaction was terminated by rapid filtration through presoaked (0.5% poylethyleneimine) filters using 48R Brandel Cell Harvester (Gaithersburg, Md.).

Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H] 5-HT averaged between 45-50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation. *Biochem. Pharmacol.*, 22:3099-3108 (1973). All experiments were performed in triplicate. Representative compounds of the present invention were found to have high affinity for the 5-HT$_{1F}$ receptor as measured by the procedure described above, as for example $K_i$'s of less than or equal to 300 nM. Preferred compounds of the present invention have $K_i$'s of less than or equal to 100 nM. A yet more preferred embodiment provides compounds having a $K_i$ of less than or equal to 50 nM.

Selectivity for the 5-HT$_{1F}$ Receptor

Compounds of the prevent invention are relatively selective for the 5-HT$_{1F}$ receptor, particularly in comparison to other 5-HT receptor subtypes, specifically other receptors in the 5-HT$_1$ subclass, as for example, but without limitation, the 5-HT$_{1A}$, 5-HT$_{1B}$, 5-HT$_{1D}$, and 5-HT$_{1E}$ receptor subtypes. Affinity for these other receptor subtypes can readily be determined by slight modification of the above described radioligand receptor binding assays using cells transfected with the desired receptor subtype in place of cells transfected with the 5-HT$_{1F}$ receptor subtype. The binding affinities of representative compounds of the present invention were determined by such assays and were found to be selective for the 5-HT$_{1F}$ receptor; that is the affinities of the compounds for the 5-HT$_{1F}$ receptor were on the whole, higher than for other receptor subtypes, particular for the 5-HT$_{1B}$ and 5-HT$_{1D}$ receptor subtypes.

Measurement of cAMP Formation

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. N. Adham, et al., supra,; R. L. Weinshank, et al., *Proceedings of the National Academy of Sciences* (USA), 89:3630-3634, 1992; and the references cited therein.

Human 5-HT$_{1F}$ receptor transfected NIH3T3 cells (estimated $B_{max}$ from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% $CO_2$. Drug dose-effect curves were then conducted by adding 6 different final concentrations of drug, followed immediately by the addition of forskolin (10 µM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 µM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the present invention were tested and found to be agonists of the 5-HT$_{1F}$ receptor in the cAMP assay described above.

Protein Extravasation Assay

The following test was performed to determine the ability of compounds of the present invention to inhibit protein extravasation, which test is also a functional assay for the neuronal mechanism of migraine.

Harlan Sprague-Dawley rats (225-325 g) or guinea pigs from Charles River Laboratories (225-325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the ends (Rhodes Medical Systems, Inc.), were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were coverslipped with a 70% glycerol/water solution.

A fluorescence microscope (Zeiss) equipped with a grating monchromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 µm steps) on each dural sample. The mean and standard deviation of the measurements were determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. Representative compounds of the present invention were assayed by the above procedure and were found to significantly inhibit neuronal protein extravasation.

Rabbit Saphenous Vein Contraction

Representative compounds of the present invention were tested in a rabbit saphenous vein contraction assay to measure their ability to mediate vasoconstriction.

Male New Zealand White rabbits (3-6 lbs) (Hazleton, Kalamazoo, Mich.) were sacrificed by a lethal dose of sodium pentobarbital (325 mg) injected into the ear vein. Tissues were dissected free of connective tissue, cannulated in situ with polyethylene tubing (PESO, outside diameter=0.97 mm) and placed in petri dishes containing modified Kreb's solution (described infra). The tips of two 30-gauge stainless steel hypodermic needles bent into an L-shape were slipped into the polyetylene tubing. Vessels were gently pushed from the cannula onto the needles. The needles were then separated so that the lower one was attached with thread to a stationary glass rod and the upper one was tied with thread to the transducer.

Tissues were mounted in organ baths containing 10 mL of modified Krebs' solution of the following composition: 118.2 mMol NaCl, 4.6 mMol KCl, 1.6 mMol $CaCl_2.H_2O$, 1.2 mMol $KH_2PO_4$, 1.2 mMol $MgSO_4$, 10.0 mMol dextrose and 24.8 mMol $NaHCO_3$. Tissue bath solutions were maintained at 37° C. and aerated with 95% $O_2$ and 5% $CO_2$. An initial optimum resting force of 1 gm was applied to the saphenous vein. Isometric contractions were recorded as changes in grams of force on a Beckman Dynograph with Statham UC-3 transducers and microscale accessory attachments. Tissues were allowed to equilibrate 1 to 2 hours before exposure to drugs. Cumulative agonist concentration-response curves were generated in tissues and no tissue was used to generate more than two agonist concentration-response curves. Results are expressed as a mean $EC_{50}$ and the maximal response expressed as a percentage of the maximal tissue contraction response to 67 mM KCl administered initially to each tissue.

This vasoconstriction assay measures two important parameters, saphenous vein contraction ($EC_{50}$) and maximal contraction as a % maximal KCl response ($\%_{max}$ KCl). The saphenous vein contraction ($EC_{50}$) is a measure of the dose required to contract tissue to 50% of the maximal response that the specific compound is capable of mediating. The maximal response that the saphenous vein is capable of exhibiting is measured after administration of a high concentration (67 mM) of KCl. The % maximal KCl contraction is the ratio of the maximal response that the specific compound is capable of mediating divided by the maximal response that the tissue can produce upon stimulation with KCl. For purposes of this application, a compound may be considered to not have significant vasoconstrictive activity if it produces a maximal contraction of less than or equal to 5% of the contraction produced by the 67 mM KCl positive control at compound concentrations of up to 100 μM.

Representative compounds of the present invention were tested with the above saphenous vein assay and found to not be significantly vasoconstrictive. This contrasts greatly with prior art compounds for the treatment of migraine targeting the neural vasoconstrictive model for migraine treatment, which compounds were selected on the basis of strong vasoconstrictive activity, as for example, sumatriptan, which has an $EC_{50}$ of 0.66 mM and a $\%_{max}$ KCl of 64.20 in this assay.

Specifidity Index

The specificity of compounds of the present invention for 5-$HT_{1F}$ mediated inhibition of neuronal protein extravasation versus vasoconstrictive activity can be expressed with a Specificity Index, which is the ratio of vasoconstriction to efficacy in inhibiting neuronal protein extravasation:

$$\text{Specificity Index} = \frac{\text{Corrected Vasconstriction } EC_{50} \text{ (M)}}{\text{Extravasation } ID_{50} \text{ (mMol/kg)}}$$

The Corrected Vasoconstriction takes into consideration the maximal contraction relative to KCl for each individual compound, and is defined as the vasoconstriction $EC_{50}$ value divided by the $\%_{max}$ KCl.

For example, sumatriptan has a corrected vasoconstriction $EC_{50}$ of $1.03 \times 10^{-8}$ M (0.66 mM $EC_{50} \div 64.20\%_{max}$ KCl) and an extravasation inhibition $ID_{50}$ of $2.6 \times 10^{-8}$ mMol/Kg, giving a Specificity Index of 0.40.

Thus the procedure for determining the Specificity Index of any given compound is as follows:

1. Measure the affinity of the compound for the 5-$HT_{1F}$ receptor using the radioligand binding method described above;
2. Once affinity for the 5-$HT_{1F}$ receptor is established, determine whether the compound is an agonist, partial agonist or antagonist of the 5-$HT_{1F}$ receptor by its response in the above described cAMP assay;
3. If the compound is shown to be an agonist or partial agonist with an $E_{max}$ of at least about 50%, measure efficacy of the compound in inhibition of protein extravasation and saphenous vein contraction using the above described assays; and
4. Calculate the Specificity Index as shown above.

While compounds with a Specificity Index greater than 1 are useful for the methods and uses of the present invention, larger values for the Specificity Index are preferred. A larger Specificity Index indicates greater specificity for efficacy in inhibition of neuronal protein extravasation over vasoconstriction. Thus, preferred compounds have a Specificity Index of greater than or equal to 10 (at least 10), preferably greater than or equal to 100 (at least 100). More preferred compounds have a Specificity Index of greater than or equal to 1000 (at least 1000), and yet more preferred compounds have Specificity Indexes greater than or equal to 5000 (at least 5000).

Formulations

The type of formulation used for the administration of the compounds employed in the methods of the present invention may be dictated by the particular compounds selected, the type of pharmacokinetic profile desired from the route of administration, and the state of the patient.

Formulations amenable to oral, sublingual, nasal or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, gels, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh. In one embodiment of the present invention, the particle size range is between about 0.1 μm to about 100 μm.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a compound of formula I.

Formulation Example 1

Hard Gelatin Capsules

| Ingredient | Quantity (mg/capsule) |
|---|---|
| 2,4,6-Trifluoro-N-[6-(1-methyl-piperidine-4-carbonyl)-pyridin-2-yl]-benzamide hydrochloric acid salt | 30.0 |
| Starch | 305.0 |
| Magnesium stearate | 5.0 |

The above ingredients are mixed and filled into hard gelatin capsules in 340 mg quantities.

Formulation Example 2

Tablet

| Ingredient | Quantity (mg/tablet) |
|---|---|
| 2-Chloro-6-fluoro-N-[6-(1-methyl-piperidine-4-carbonyl)-pyridin-2-yl]-benzamide mono-hydrochloric acid salt | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

Dry Powder Inhaler

| Ingredient | Weight % |
|---|---|
| 2,4,6-Trifluoro-N-methyl-N-[6-(piperidine-4-carbonyl)-pyridin-2-yl]-benzamide | 5 |
| Lactose | 95 |

The active ingredient is mixed with the lactose and the mixture is added to a dry powder inhaling appliance.

Formulation Example 4

Tablet

| Ingredient | Quantity (mg/tablet) |
|---|---|
| 2-Fluoro-N-[6-(1-methyl-piperidine-4-carbonyl)-pyridin-2-yl]-isonicotinamide | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules

| Ingredient | Quantity (mg/capsule) |
|---|---|
| Furan-3-carboxylic acid[6-(1-methyl-piperidine-4-carbonyl)-pyridin-2-yl]-amide | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suspensions

| Ingredient | Amount |
| --- | --- |
| 4-Fluoro-N-[6-(1-methyl-piperidine-4-carbonyl)-pyridin-2-yl]-2-trifluoromethyl-benzamide mono-hydrochloric acid salt | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 7

Capsules

| Ingredient | Quantity (mg/capsule) |
| --- | --- |
| 4-Chloro-2-methoxy-N-[6-(1-methyl-piperidine-4-carbonyl)-pyridin-2-yl]-benzamide | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 8

Intravenous Formulation

| Ingredient | Quantity |
| --- | --- |
| 2-Ethoxy-N-[6-(1-methyl-piperidine-4-carbonyl)-pyridin-2-yl]-benzamide | 250.0 mg |
| Isotonic saline | 1000 ml |

Formulation Example 9

Sublingual or Buccal Tablets

| Ingredient | Quantity (mg/tablet) |
| --- | --- |
| 2,4,6-Trifluoro-N-[6-(1-methyl-piperidine-4-carbonyl)-pyridin-2-yl]-benzamide hemi-succinnic acid salt | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the active ingredient is slowly admixed. The homogenous mixture is poured into forms made of an inert material to produce a drug-containing diffusion matrix having a thickness of about 2-4 mm. This diffusion matrix is then cut to form individual tablets having the appropriate size.

Formulation Example 9

Sublingual or Buccal Tablets

| Ingredient | Quantity (mg/tablet) |
| --- | --- |
| 2,4,6-Trifluoro-N-[6-(1-methyl-piperidine-4-carbonyl)-pyridin-2-yl]-benzamide hemi-succinnic acid salt | 5.0 (freebase equivalent) |
| Mannitol | 20 |
| Gelatine | 2.0 |
| Water add to total volume of | 100 μL |
| Total | 27.0 mg |

The compound was dissolved in water containing 20% mannitol and 2% gelatine to provide a stock solution at a concentration of 50 mg/mL (free base equivalent). The solution was aliquoted into forms holding 100 μL solution each. The formulation was then frozen at −20° C. for 3 hours and freeze dried.

Formulation Example 8

Intravenous Formulation

| Ingredient | Quantity per 1.0 mL Formulation |
| --- | --- |
| 2,4,6-Trifluoro-N-[6-(1-methyl-piperidine-4-carbonyl)-pyridin-2-yl]-benzamide hemi-succinnic acid salt | 1.16 mg |
| Mannitol parenteral | 50.0 mg |
| Water for injection: q.s. to | 1.0 mL |

The compound and mannitol are dissolved in water and then water is added to obtain the desired final volume. The solution is then sterile filtered and aseptically filled into suitable vials.

While it is possible to administer a compound employed in the methods of this invention directly without any formulation, the compounds are usually administered in the form of pharmaceutical formulations comprising a pharmaceutically acceptable excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

In one preferred embodiment of the present invention, there is provided a pharmaceutical formulation comprising at lest one active compound as described above in a formulation adapted for buccal and/or sublingual, or nasal administration. This embodiment provides administration of the active compound in a manner that avoids gastric complications, such as first pass metabolism by the gastric system and/or through the liver. This administration route may also reduce adsorption times, providing more rapid onset of therapeutic benefit. The compounds of the present invention may provide particularly favorable solubility profiles to facilitate sublingual/buccal formulations. Such formulations typically require relatively high concentrations of active ingredients to deliver sufficient amounts of active ingredients to the limited surface area of the sublingual/buccal mucosa for the relatively short durations the formulation is in contact with the surface area, to allow the absorption of the active ingredient. Thus, the very high activity of the compounds of the present invention combined with their high solubilities, facilitate their suitability for sublingual/buccal formulation.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

What is claimed is:

1. A method for the treatment of migraine in a mammal comprising administering to a mammal in need of such treatment an effective amount of 2,4,6-trifluoro-N-[6-[(1-methyl-4-piperidinyl)carbonyl]-2-pyridinyl]-benzamide or a pharmaceutically acceptable acid addition salt thereof.

2. A method for the treatment of migraine in a mammal comprising administering to a mammal in need of such treatment an effective amount of 2,4,6-trifluoro-N-[6-[(1-methyl-4-piperidinyl)carbonyl]-2-pyridinyl]-benzamide hydrochloride salt.

3. A method for the treatment of migraine in a mammal comprising administering to a mammal in need of such treatment an effective amount of 2,4,6-trifluoro-N-[6-[(1-methyl-4-piperidinyl)carbonyl]-2-pyridinyl]-benzamide hydrochloride salt.

* * * * *

UNITED STATES PATENT AND TRADEMARK OFFICE
CERTIFICATE OF CORRECTION

PATENT NO. : 8,748,459 B2  
APPLICATION NO. : 13/363895  
DATED : June 10, 2014  
INVENTOR(S) : Michael Philip Cohen et al.

Page 1 of 1

It is certified that error appears in the above-identified patent and that said Letters Patent is hereby corrected as shown below:

In the Claims

Column 68, claim 2, lines 43-44, replace "hydrochloride" with --hemisuccinate--.

Signed and Sealed this  
Fifth Day of August, 2014

Michelle K. Lee  
*Deputy Director of the United States Patent and Trademark Office*